(12) United States Patent
Yeo et al.

(10) Patent No.: US 12,236,014 B2
(45) Date of Patent: Feb. 25, 2025

(54) WIRELESS SOFT SCALP ELECTRONICS AND VIRTUAL REALITY SYSTEM FOR BRAIN-MACHINE INTERFACES

(71) Applicants: GEORGIA TECH RESEARCH CORPORATION, Atlanta, GA (US); Woon-Hong Yeo, Atlanta, GA (US); Musa Mahmood, Atlanta, GA (US)

(72) Inventors: Woon-Hong Yeo, Atlanta, GA (US); Musa Mahmood, Atlanta, GA (US)

(73) Assignee: GEORGIA TECH RESEARCH CORPORATION, Atlanta, GA (US)

(*) Notice: Subject to any disclaimer, the term of this patent is extended or adjusted under 35 U.S.C. 154(b) by 0 days.

(21) Appl. No.: 18/563,788

(22) PCT Filed: May 27, 2022

(86) PCT No.: PCT/US2022/031432
§ 371 (c)(1),
(2) Date: Nov. 22, 2023

(87) PCT Pub. No.: WO2022/251696
PCT Pub. Date: Dec. 1, 2022

(65) Prior Publication Data
US 2024/0427418 A1    Dec. 26, 2024

Related U.S. Application Data

(60) Provisional application No. 63/311,628, filed on Feb. 18, 2022, provisional application No. 63/194,111, filed on May 27, 2021.

(51) Int. Cl.
*G06F 3/01*    (2006.01)
*G06N 3/0464*  (2023.01)

(52) U.S. Cl.
CPC .......... *G06F 3/015* (2013.01); *G06N 3/0464* (2023.01)

(58) Field of Classification Search
CPC ............................ G06F 3/015; G06N 3/0464
See application file for complete search history.

(56) References Cited

U.S. PATENT DOCUMENTS 11,907,421 B1 * 2/2024 Clements ............... G06F 3/012
11,995,233 B2 * 5/2024 Yang ....................... A63F 13/53
(Continued)

FOREIGN PATENT DOCUMENTS

WO  WO-2017007271 A1 *  1/2017
WO  WO-2020147556 A1 *  7/2020
WO  WO-2022251696 A1 * 12/2022 ............... A61B 5/16

OTHER PUBLICATIONS

International Search Report and Written Opinion received in PCT/US2022/031432 mailed Sep. 1, 2022.

*Primary Examiner* — William Lu
(74) *Attorney, Agent, or Firm* — Meunier Carlin & Curfman LLC

(57) ABSTRACT

An exemplary wireless soft scalp electronic system and method are disclosed that can actuate commands for a brain-machine interface (BMI) or brain-computer-interface (BCI) by performing real-time, continuous classification. e.g., via a trained neural network, of motor imagery (MI) brain signals or of steady-state visually evoked potential (SSVEP) signals. In some embodiments, the exemplary system is configured as a low-profile, portable system that includes microneedle electrodes that can acquire EEG signals for a brain-machine interface controller. The microneedle electrodes may be configured as soft imperceptible gel-less epidermis-penetrating microneedle electrodes that can provide improved contact surface area and reduced electrode impedance density, e.g., to enhance EEG signals (Continued)

and the signal classification accuracy. The microneedle electrodes can be further integrated with soft electronics that can be mounted locally in proximity to the electrodes to reduce obtrusive wiring and improve signal acquisition quality.

20 Claims, 22 Drawing Sheets

(56) References Cited

U.S. PATENT DOCUMENTS

| | | |
|---|---|---|
| 2010/0106041 A1 | 4/2010 | Ghovanloo et al. |
| 2015/0335288 A1* | 11/2015 | Toth .................... A61B 5/6833 |
| | | 600/391 |
| 2015/0351690 A1 | 12/2015 | Toth et al. |
| 2017/0231490 A1 | 8/2017 | Toth et al. |
| 2019/0183430 A1* | 6/2019 | Alphonse ................ A61B 5/22 |
| 2019/0206558 A1* | 7/2019 | Hyde ..................... G16H 40/20 |
| 2019/0247650 A1* | 8/2019 | Tran .................... A61N 1/3704 |
| 2020/0201434 A1* | 6/2020 | Aliamiri ................ G06N 3/088 |
| 2021/0378582 A1* | 12/2021 | Day ........................ A61B 5/38 |
| 2023/0240608 A1* | 8/2023 | Khaleghimeybodi ...................... |
| | | A61B 5/0205 |
| | | 600/301 |

\* cited by examiner

| Reference | Year | Accuracy (%) | Length (second) | Class (number) | Channel (number) | ITR (bits/min) |
|---|---|---|---|---|---|---|
| This work | 2022 | 78.93 ± 1.05 | 0.8 | 33 | 4 | 243.6 ± 12.5 |
| (Mahmood et al. 2019) | 2019 | 94.54 | 0.94 | 5 | 2 | 122.1 ± 3.53 |
| (Nakanishi et al. 2017) | 2018 | 89.83 | 0.8 | 40 | 9 | 325.33 ± 38.2 |
| (Xing et al. 2018) | 2018 | 93.2 | 1 | 12 | 8 | 92.35 |
| (Kwak et al. 2017) | 2017 | 99.19 | 2 | 5 | 8 | 67.13* |
| (Chen et al. 2015) | 2015 | 91.09 | 1 | 40 | 9 | 270.0 ± 61.8 |
| (Volosyak 2011) | 2011 | 96.79 | 2 | 5 | 8 | 61.70 ± 32.7 |
| (Wang et al. 2010) | 2010 | 97.20 | 3.08 | 16 | 10 | 72.2 |

WIRELESS SOFT SCALP ELECTRONICS AND VIRTUAL REALITY SYSTEM FOR BRAIN-MACHINE INTERFACES

RELATED APPLICATION

This application is a U.S. National Stage application filed under 35 U.S.C. § 371 of PCT/US2022/031432, filed May 27, 2022, which claims priority to, and the benefit of, U.S. Provisional Application No. 63/194,111, filed May 27, 2021, entitled "WIRELESS SOFT SCALP ELECTRONICS AND VIRTUAL REALITY SYSTEM FOR MOTOR IMAGERY-BASED BRAIN-MACHINE INTERFACES," and U.S. Provisional Application No. 63/311,628, filed Feb. 18, 2022, entitled, "VIRTUAL REALITY (VR)-ENABLED BRAIN-COMPUTER INTERFACES VIA WIRELESS SOFT BIO-ELECTRONICS," each of which is hereby incorporated herein by reference in its entirety.

STATEMENT OF GOVERNMENT INTEREST

This invention was made with government support under grant no. R21AG064309 awarded by the National Institute of Health. The government has certain rights in the invention.

BACKGROUND

Motor imagery electroencephalography (MI) refers to the mental simulation of body movements by consciously accessing aspects of body movement to provide a mechanism for brain-machine interfaces. Conventional electroencephalography (EEG) for motor imagery typically employs a hair cap with multiple wired electrodes and gels that involve extensive setup time and are uncomfortable to use. While the latest EEG designs are trending toward wireless, wearable EEG for day-to-day mobile EEG monitoring, they nevertheless continue to employ rigid, bulky circuitries and gel-based skin-contact electrodes that are of an obtrusive nature, providing low information throughput due to noise-prone brain signal detection, and have limited recording channels.

Similar EEG hardware can also be used for the acquisition of steady-state visually evoked potentials (SSVEP), which are brain signals that are natural responses to visual stimulation at specific frequencies. When the retina is excited, for example, by a visual stimulus ranging from 3.5 Hz to 75 Hz, the brain can generate electrical activity at the same (or multiples of) frequency of the visual stimulus.

There are benefits to the improvements of brain-machine interface (BMI) hardware and BMI applications.

SUMMARY

An exemplary wireless soft scalp electronic system and method are disclosed that can actuate commands for a brain-machine interface (BMI) or brain-computer-interface (BCI) by performing real-time, continuous classification, e.g., via a trained neural network, of motor imagery (MI) brain signals or of steady-state visually evoked potential (SSVEP) signals.

In some embodiments, the exemplary system is configured as a low-profile, portable system that includes microneedle electrodes that can acquire EEG signals for a brain-machine interface controller. The microneedle electrodes may be configured as soft imperceptible gel-less epidermis-penetrating microneedle electrodes that can provide improved contact surface area and reduced electrode impedance density, e.g., to enhance EEG signals and the signal classification accuracy. The microneedle electrodes can be further integrated with soft electronics that can be mounted locally in proximity to the electrodes to reduce obtrusive wiring and improve signal acquisition quality.

The exemplary wireless soft scalp electronic system and method can operate in combination with a virtual reality (VR) or augmented reality (AR) training system comprising a VR/AR environment controller to provide clear, consistent visuals and instant biofeedback to a user in a MI or SSVEP application. In some embodiments, the VR/AR environment controller can employ the acquired and classified EEG signals to actuate a command that renders an object VR/AR scene associated with motor imagery (e.g., one or more body objects that can perform aspects of body movement) to be viewed by a user as feedback to the user during the MI training. The VR/AR hardware and brain-machine interface hardware can be used to provide and acquire visual stimuli for the acquisition of steady-state visually evoked potentials. The VR/AR hardware and associated training can reduce the variance in detectable EEG response, e.g., in MI and SSVEP applications. In a study reported herein, the scalp electronic system and associated training were observed to provide a high classification accuracy for motor imagery applications (93.22±1.33% for four classes), allowing wireless, real-time control of a virtual reality game.

In an aspect, a system is disclosed, including an electroencephalography-based (EEG) brain-machine interface. The system can include a set of low-profile EEG sensors each comprising an array of flexible epidermis-penetrating microneedle electrodes fabricated on a flexible-circuit substrate, the flexible-circuit substrate operatively connected to an analog-to-digital converter circuitry operatively connected to a wireless interface circuitry; and a brain-machine interface operatively connected to the set of low-profile EEG sensors, the brain-machine interface comprising: a processor; and a memory operatively connected to the processor, the memory having instructions stored thereon, where execution of the instructions by the processor causes the processor to: receive EEG signals acquired from the low-profile EEG sensor; continuously classify brain signals as control signals via a trained neural network from the acquired EEG signals; and output the control signals to a virtual reality environment controller to actuate a command (e.g., for training) in a VR scene generated by the virtual reality environment controller be viewed by the subject.

In some embodiments, the command causes a set of movements of an extremity in the VR scene, and where the trained neural network is configured to classify the brain signals for the set of movements.

In some embodiments, the set of low-profile EEG sensors is connected to the brain-machine interface over a set of stretchable flexible connectors.

In some embodiments, the microneedle electrodes have expanded contact surface area and reduced electrode impedance density.

In some embodiments, the system further includes a wearable soft headset comprising a low-modulus elastomeric band.

In some embodiments, the trained neural network includes a spatial convolutional neural network.

In some embodiments, the set of low-profile EEG sensors is placed along the scalp for motor imagery.

In some embodiments, the set of low-profile EEG sensors is placed along the scalp for steady-state visually evoked potentials (SSVEP) measurements.

In some embodiments, the virtual reality environment controller to configured to generate split-eye asynchronous stimulus (SEAS) in the virtual scene for a real-time text speller interface.

In some embodiments, the execution of the instructions by the processor further causes the processor to transmit the acquired EEG signals to a remote or cloud computing device executing a retraining operation of the trained neural network; and receive during the run-time operation of the virtual reality environment controller an updated trained neural network from the remote or cloud computing device.

In some embodiments, a plurality of the flexible epidermis-penetrating microneedle electrodes of the array each is at least 500 µm in height (e.g., 800 µm) to mount on a hairy scalp with a base width of about 350 µm and has an area of about 36 mm2.

In an aspect, a method is disclosed. The method can include providing a set of low-profile EEG sensors placed at a scalp of a user, where the set of low-profile EEG sensors each includes an array of flexible epidermis-penetrating microneedle electrodes fabricated on a flexible-circuit substrate, the flexible-circuit substrate operatively connected to an analog-to-digital converter circuitry operatively connected to a wireless interface circuitry; receiving, by a processor or a brain-machine interface operatively connected to the set of low-profile EEG sensors, EEG signals acquired from the low-profile EEG sensor; continuously classifying, by the processor, brain signals as control signals via a trained neural network from the acquired EEG signals; and outputting, by the processor, the control signals to a virtual reality environment controller to actuate a command in a VR scene generated by the virtual reality environment controller be viewed by the subject.

In some embodiments, the set of low-profile EEG sensors is placed directly on the scalp without conductive gel or paste.

In some embodiments, the set of low-profile EEG sensors includes i) a reference array of flexible epidermis-penetrating microneedle electrodes placed at an apex position on the scalp and ii) six arrays of flexible epidermis-penetrating microneedle electrodes releasably attached to a low-modulus elastomeric band at a first frontal position, a second back position, and at four side positions for motor imagery measurements.

In some embodiments, the set of low-profile EEG sensors includes i) a reference array of flexible epidermis-penetrating microneedle electrodes placed at a back position on the scalp and ii) four arrays of flexible epidermis-penetrating microneedle electrodes releasably attached to a low-modulus elastomeric band at a back region of the scalp for steady-state visually evoked potentials (SSVEP) measurements.

In some embodiments, the method can further include transmitting, by the processor, the acquired EEG signals to a remote or cloud computing device executing a retraining operation of the trained neural network; and receiving, by the processor, during run-time operation of the virtual reality environment controller an updated trained neural network from the remote or cloud computing device.

In another aspect, a non-transitory computer readable medium is disclosed. The A non-transitory computer-readable medium can have instructions stored thereon, where execution of the instructions by a processor of a brain-machine interface controller causes the processor to: receive EEG signals acquired from a set of low-profile EEG sensors placed at a scalp of a user, where the set of low-profile EEG sensors each includes an array of flexible epidermis-penetrating microneedle electrodes fabricated on a flexible-circuit substrate, the flexible-circuit substrate operatively connected to an analog-to-digital converter circuitry operatively connected to a wireless interface circuitry, where the set of low-profile EEG sensors are placed directly on the scalp without conductive gel or paste; continuously classify brain signals as control signals via a trained neural network from the acquired EEG signals; and output the control signals to a virtual reality environment controller to actuate a command in a VR scene generated by the virtual reality environment controller be viewed by the subject.

In some embodiments, the set of low-profile EEG sensors includes i) a reference array of flexible epidermis-penetrating microneedle electrodes placed at an apex position on the scalp and ii) six arrays of flexible epidermis-penetrating microneedle electrodes releasably attached to a low-modulus elastomeric band at a first frontal position, a second back position, and at four side positions for motor imagery measurements.

In some embodiments, the set of low-profile EEG sensors includes i) a reference array of flexible epidermis-penetrating microneedle electrodes placed at a back position on the scalp and ii) four arrays of flexible epidermis-penetrating microneedle electrodes releasably attached to a low-modulus elastomeric band at a back region of the scalp for steady-state visually evoked potentials (SSVEP) measurements.

In some embodiments, the execution of the instructions further causes the processor to transmit the acquired EEG signals to a remote or cloud computing device executing a retraining operation of the trained neural network; and receive during run-time operation of the virtual reality environment controller an updated trained neural network from the remote or cloud computing device.

BRIEF DESCRIPTION OF THE DRAWINGS

The skilled person in the art will understand that the drawings described below are for illustration purposes only.

DETAILED SPECIFICATION

Some references, which may include various patents, patent applications, and publications, are cited in a reference list and discussed in the disclosure provided herein. The citation and/or discussion of such references is provided merely to clarify the description of the disclosed technology and is not an admission that any such reference is "prior art" to any aspects of the disclosed technology described herein. In terms of notation, "[n]" corresponds to the nth reference in the list. For example, [1] refers to the first reference in the list. All references cited and discussed in this specification are incorporated herein by reference in their entireties and to the same extent as if each reference was individually incorporated by reference.

Example System

Figure 1:
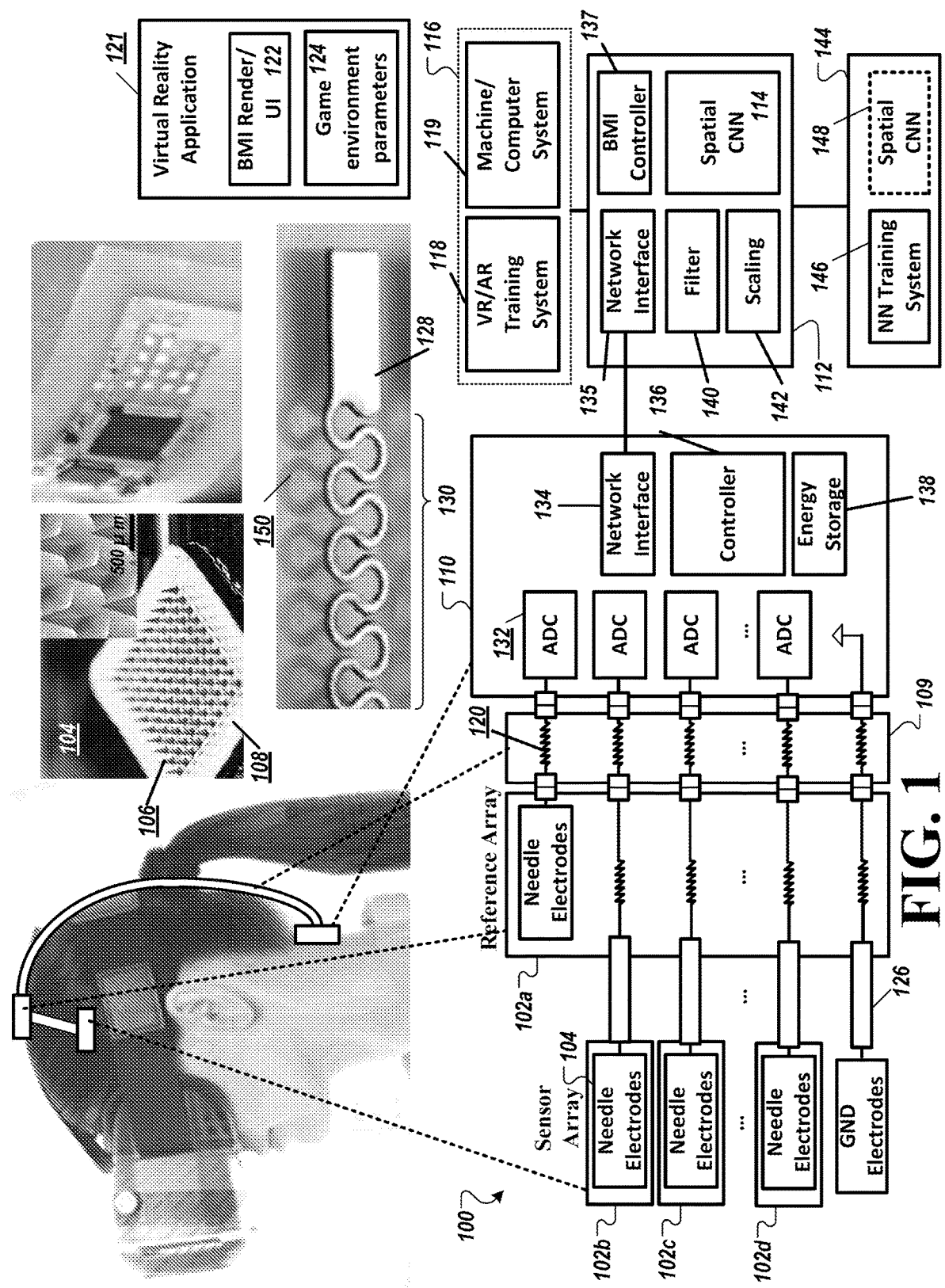
FIG. 1 shows an example electroencephalography-based brain-machine-interface system in accordance with an illustrative embodiment.

FIG. 1 shows an example electroencephalography-based (EEG) brain-machine-interface system 100 ("EEG BMI" system 100) in accordance with an illustrative embodiment. The system 100 includes a set of low-profile EEG sensors 102 (shown as 102a, 102b, 102c, 102d), each comprising an array 104 of flexible epidermis-penetrating microneedle electrodes 106 fabricated on a flexible-circuit substrate 108. In the example shown in FIG. 1, the first EEG sensor 102a is shown as a reference electrode that is connected, via a flexible connector 109, to a flexible front-end electronics assembly 110 that interfaces with a BMI control system 112 that classifies, via a neural network 114 (shown as "Spatial CNN" 114), to generate control signals to a computing device or a machine 116. The computing device or machine 116 can include a VR/AR training system 118 and/or a machine computer system 119. In turn, the VR/AR training system 118 and/or the machine/computer system 119 can be configured to execute a VR/AR application 121. The virtual reality application 121 can include a BMI rendering and UI module 122 and a module containing game environment parameters 124. The term "VR/AR" refers to a virtual reality system, an augmented reality system, or a system capable of providing both.

The other EEG sensors (shown as "Sensor Array" 102b, 102c, 102d) are measured, via the hardware or software, in relation to the reference sensor 102a and, in the example of FIG. 1, are connected via the flexible cabling 126 through the reference EEG sensor assembly 102a. The system 100 may employ more than one reference sensor assembly (e.g., 102a).

The flexible cabling 126, in the example of FIG. 1, includes a set of laser-machined stretchable and flexible interconnects 128. The interconnects 128 can have electrical conductors formed in a meandering or serpentine pattern 130 that allows the interconnects 128 to be stretched or bent. The flexible connector 109 connects the flexible assembly of the reference sensor 102a to the flexible front-end electronics assembly 110.

The flexible front-end electronics assembly 110 can include one or more analog to digital converters 132 operably connected to the array 104 of needle electrodes 102b 102c 102d through the flexible cable 126. The ADCs 132 can convert analog signals from the reference array of needle electrodes 102a and from the sensor array (e.g., 102b, 102c, 102d) to digital signals. The digital signals can be transmitted by the network interface 134 to the network interface 135 in the BMI control system 112. Additionally, the flexible front-end electronics assembly 110 can include a controller 136 that can be configured to control the operation of the energy storage 138, ADCs 132, and network interface 134.

The BMI control system 112 is configured to continuously classify brain signals as control signals via the trained neural network from the acquired EEG signals. The BMI control system 112 can provide the control signal to a machine 119, e.g., to operate a vehicle (e.g., power wheelchair) or a robotic limb, or the like.

The BMI control system 112 can include a trained neural network 114, a network interface 135, a controller 137, a filter module 140, and a scaling module 142. The trained neural network 114 is configured to classify the acquired EEG signals to generate control signals to the computing device or machine 116. In the example shown in FIG. 1, the trained neural network 114 is configured as a spatial CNN. The trained neural network can be configured as other CNN and AI systems, e.g., as described or referenced herein.

In some embodiments, the BMI control system 112 is configured to be re-configured during run-time operation. In the example shown in FIG. 1, the BMI control system is shown connected to a cloud system 144 configured with a neural network training system 146. The cloud system 144 is configured to receive the acquired EEG signals from the BMI control system 112 and re-train a local version of the neural network 114. The neural network training system 146 determines if the retrained neural network 148 improves upon the prior neural network 114. Upon such a determination, the neural network training system 146 provides the retrained neural network 148 to the BMI control system 112, which replaces (e.g., via its controller 137) the neural network 114 with the updated version.

To provide the EEG signals for the classification, BMI control system 112 includes the network interface 135 to communicate and receive from the network interface 134 of the flexible front-end electronics assembly 110. The filter module 140 and scaling module 142 are configured to preprocess the acquired EEG signals prior to the classification operation. In some embodiments, the filter module 140 is configured to filter the acquired EEG data, e.g., using a Butterworth bandpass filter, and the scaling module 142 is configured to upscale the filtered EEG data, e.g., using a linear upscaling operator.

In the example shown in FIG. 1, the BMI control system 112 can be configured to operate with a VR/AR training system 118 comprising a VR/AR environment controller (not shown) that can employ the classified control signal to actuate a set of commands in the VR scene to be displayed to the user. The VR/AR environment can be implemented using a VR/AR headset and VR/AR software. The VR/AR environment may operate with a VR software (e.g., Unity) to configure a computing device to display VR/AR graphics in a VR/AR headset. The VR/AR headset (e.g., Samsung Gear VR) may be connected to a smartphone. In an example implementation, the VR software may render 3D models (Maya) of the hands and feet, or other geometric objects, to facilitate visualization of the MI.

It should be understood that the animation software, VR/AR software, VR/AR headset, and various computing devices described with reference to this example implementation are all intended as non-limiting examples and that the present disclosure can be implemented using any suitable animation software, smartphone (or other computing devices), VR (or AR) headsets, and/or any AR or VR software package. Similarly, it should be understood that the game described is a non-limiting example and that embodiments of the present disclosure can be used to control and receive output from any computing device.

The computing device may include a processing unit that may be a standard programmable processor that performs arithmetic and logic operations necessary for the operation of the computing device. Multiple processors may be employed. As used herein, processing unit and processor refers to a physical hardware device that executes encoded instructions for performing functions on inputs and creating outputs, including, for example, but not limited to, microprocessors (MCUs), microcontrollers, graphical processing units (GPUs), and application-specific circuits (ASICs). Thus, while instructions may be discussed as executed by a processor, the instructions may be executed simultaneously, serially, or otherwise executed by one or multiple processors. The computing device may also include a bus or other communication mechanism for communicating information among various components of the computing device.

It should be appreciated that the logical operations described above can be implemented (1) as a sequence of computer-implemented acts or program modules running on a computing system and/or (2) as interconnected machine logic circuits or circuit modules within the computing system. The implementation is a matter of choice dependent on the performance and other requirements of the computing system. Accordingly, the logical operations described herein are referred to variously as state operations, acts, or modules. These operations, acts, and/or modules can be implemented in software, in firmware, in special purpose digital logic, in hardware, and any combination thereof. It should also be appreciated that more or fewer operations can be performed than shown in the figures and described herein. These operations can also be performed in a different order than those described herein.

One or more programs may implement or utilize the processes described in connection with the presently disclosed subject matter, e.g., through the use of an application programming interface (API), reusable controls, or the like. Such programs may be implemented in a high-level procedural or object-oriented programming language to communicate with a computer system. However, the program(s) can be implemented in assembly or machine language, if desired. In any case, the language may be a compiled or interpreted language, and it may be combined with hardware implementations.

Example #2 Motor Imagery-Based Brain-Machine Interface

Figure 2:
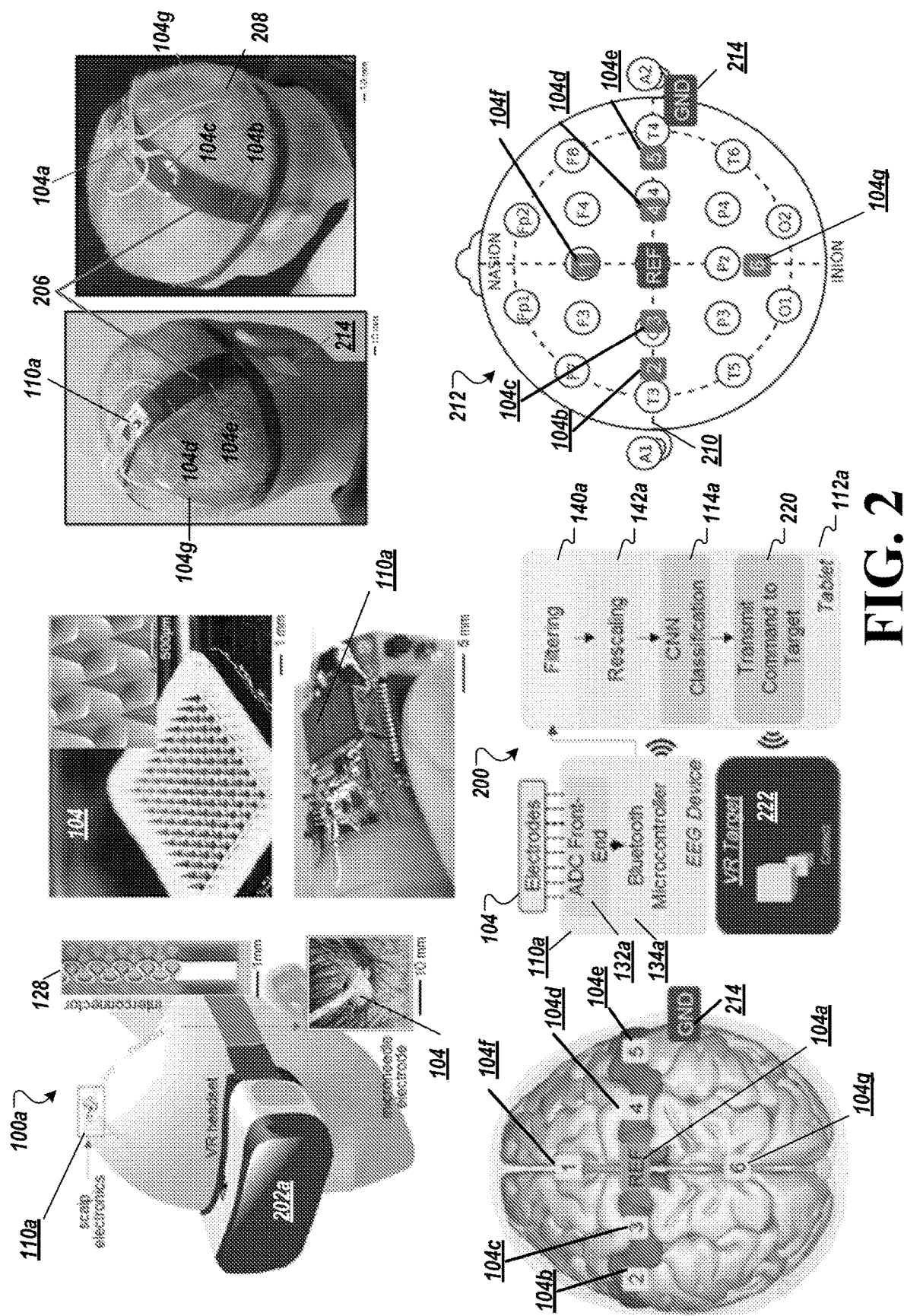
FIG. 2 shows an example EEG brain-machine-interface system configured as a low-profile EEG-sensor soft-scalp-electronics device for motor imagery (MI) training or operation in accordance with an illustrative embodiment.

FIG. 2 shows an example EEG BMI system 100 (shown as 100a) that includes the flexible front-end electronics assembly 110 (shown as 110a) configured as a low-profile EEG-sensor soft-scalp-electronics (SSE) device for motor imagery (MI) training or operation that interfaces with a VR/AR headset 202 (shown as 202a) in accordance with an illustrative embodiment. The SSE device 110a can be placed along the scalp of a user and includes (i) fully portable signal-acquisition electronics on a flexible substrate and (ii) stretchable interconnectors 128 that connect to a set of flexible microneedle arrays 104 (shown as 104a, 104b, 104c, 104d, 104e, and 104f).

The soft-scalp-electronic system 110a can be configured for MI brain signal detection for persistent BMI by continuously recording brain signals via a head-worn strap 206. The SSE system 110a is configured to provide the acquired EEC signals via a wireless connection (or via a wired connection) to an external computing device that then classifies the acquired EEG signals as signals, e.g., for MI application or for an immersive visualization training.

In the example shown in FIG. 2, the BMI system 100a includes a reduced number of EEG electrodes that are straightforward to set up to reduce setup usage complexity, e.g., as compared to conventional EEG applications, while not sacrificing classification performance.

In an aspect, in the example shown in FIG. 2, the SSE system 110a includes an array of integrated stretchable interconnectors 128 bonded to flexible microneedle electrodes (FMNEs) (e.g., 104). The soft-scalp-electronic system 110a may be fabricated using a flexible membrane circuit to have great mechanical compliance. The flexible membrane circuit can be integrated with electronic chips (e.g., front-end acquisition IC and network interface IC) and encapsulated to maintain mechanical compliance.

Each of the arrays of FMNEs (e.g., 104), in the example shown in FIG. 2, includes a set of high-aspect-ratio needles, e.g., greater than 2 (e.g., 800 μm in height with a base width of 350 μm). Other needle base to height ratios may be employed, e.g., 1, 1.1, 1.2, 1.3, 1.4, 1.5, 1.6, 1.7, 1.8, 1.9, 2.0. In some embodiments, the needle base to height ratios can be greater than 2.

The soft-scalp-electronic system 110a, in the example shown in FIG. 2, is attached or affixed to the wearable head strap 206, which may be integrated with a set of low-modulus elastomeric bands 208 that can be molded together to secure the multiple FMNEs at the MI positions on the user's scalp. The primary band 206 can wrap around the head of the user about an axial plane 210 to secure five FMNEs on the temporal lobes (reference FMNE 104a ("Cz"), first axial FMNE 104b ("C2"), second axial FMNE 104c ("C3"), third axial FMNE 104d ("C4"), and axial fourth FMNE 104e ("C5")). The primary band 208 connects, via the flexible interconnects, to an inion FMNE 104f ("Fz") and a nasion FMNE 104g ("POz") to provide 6-channels of EEC measurements with respect to the reference electrode array. A schematic of the same is shown in plot 212. Plot 212 also shows the FMNEs in relation to a standard EEG cap with 20+ electrodes. The primary band 208 also connects to a ground electrode 214 that is configured to be placed behind the ear. Other number of electrode arrays may be employed, including 7, 8, 9, 10, 11, 12, etc. In some embodiments, the number of electrode arrays can be greater than 12.

The electrode arrays (e.g., 104) are connected to ADC front-end circuitries (comprising ADCs 132, shown as 132a) of the soft-scalp-electronic system 110a. The soft-scalp-electronic system includes the network interface 134 (shown as "Bluetooth controller" 134a) that can communicate the acquired EEC signals to the BMI control system 112 (shown as "Tablet" 112a). In the example shown in FIG. 2, the BMI control system 112a is configured to process sequences from the EEG recording machine learning classification algorithm 114 (shown as "convolutional neural network" 114a) to generate MI classifications that can be used as control signals to control VR/AR targets in a VR/AR system environment. The machine computer system 120a includes a filter operation 140 (shown as 140a) and rescaling operation 142 (shown as 142a). The machine computer system 112a is configured to optimally capture event-related synchronization and desynchronization, e.g., relating to separate hands and both feet, as well as capturing overall alpha rhythm activity. The ML model can decompose spatial features from multiple dipolar sources of the motor cortex. The output of the classification can be sent as a command 220 to a target shown as a VR target 222.

Example #3 SSVEP-Based Brain-Machine Interface

Figure 3A:
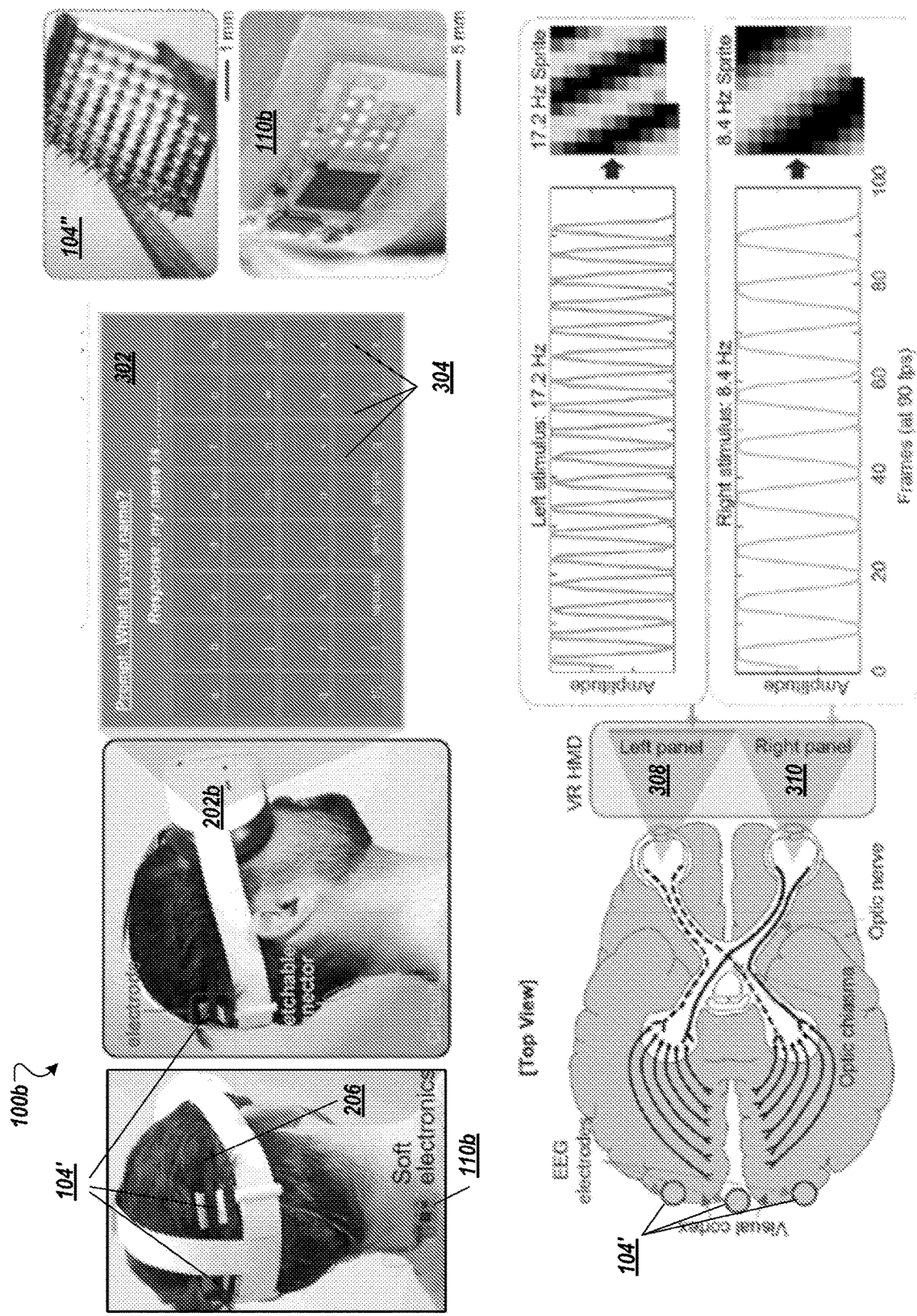
FIGS. 3A, 3B, and 3C each shows aspects of an example EEG brain-machine-interface system configured as a low-profile EEG-sensor soft-scalp-electronics device for SSVEP training or operation in accordance with an illustrative embodiment.

FIG. 3A shows an example EEG BMI system 100 (shown as 100b) that includes the flexible front-end electronics assembly 110 (shown as 110b) configured as a low-profile EEG-sensor soft-scalp-electronics (SSE) device for SSVEP training or operation that interfaces with a VR/AR headset 202 (shown as 202b) in accordance with an illustrative embodiment. The SSE device 110b can also be placed along the scalp of a user and includes (i) fully portable signal-acquisition electronics on a flexible substrate and (ii) stretchable interconnectors 128 that connect to a set of flexible microneedle arrays 104 (shown as 104', e.g., 104a', 104b', 104c', 104d', 104e'-see FIG. 3B).

To improve the brain-signal recording throughput, in the example shown in FIG. 3A, the EEG BMI system 100b is used to acquire SSVEP signals from different eye-specific stimuli being presented to each eye via split-eye asynchronous stimulus (SEAS) application. The separate eyes stimulation can produce unique asynchronous stimulus patterns that can provide more encoded channels to improve brain-signal recording throughput. The EEG BMI system 100b can be used to provide real-time monitoring of steady-state visually evoked potentials (SSVEP) for portable BCI with over 30 channels, e.g., for text spelling. In the example shown in FIG. 3A, a user interface panel 302 is presented, e.g., in a VR/AR environment, with textual elements 304 in which the textual elements 304 (a portion highlighted) include different steady-state flickering stimuli patterns. That is, each textual element 304 (32 elements) can be encoded with a unique steady-state flickering stimulus. With SEAS, the steady-state flickering stimuli patterns can be differently presently for the left and right display (shown as 308 and 310, respectively).

Figures 3B, 3C:
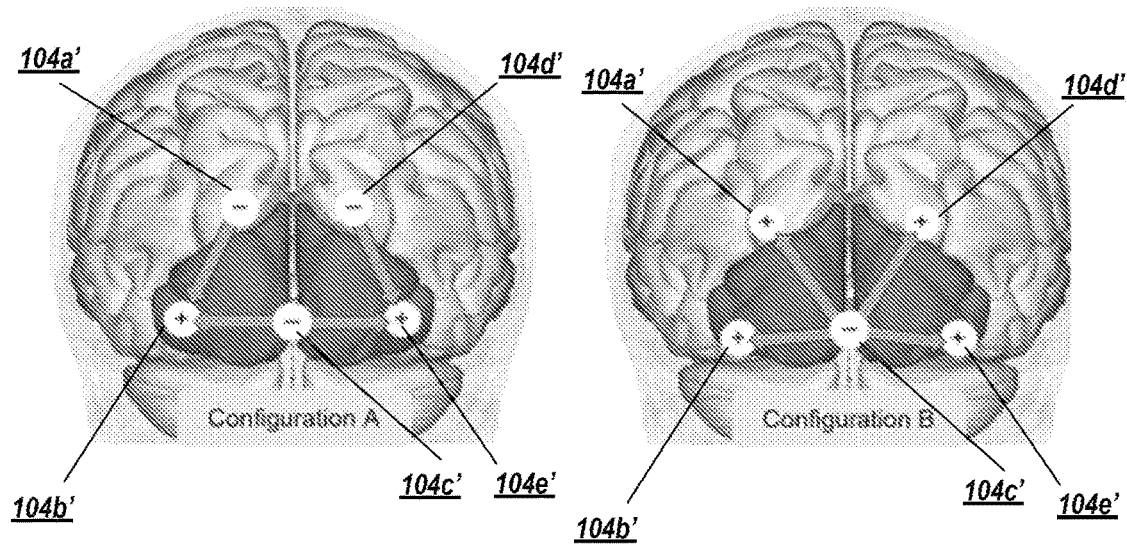

FIG. 3C shows example stimulus frequencies (312) and targets (shown as "Target Text" 314). In the example shown in FIG. 3C, the stimulus frequencies 312 are presented as either the same frequencies in both eyes (rows "1" and "3," shown as 316 and 318) or with different frequencies for the left eye and right eye (rows "2" and "4," shown as 320, 322). In rows "2" and "4" (320, 324), each of the first numbers (326) represents the frequency seen by the left eye, and each of the second numbers (328) represents the frequency seen by the right eye. Other configurations can be used. The same frequencies output, e.g., per rows "1" and "3," provide a common reference for the eye to track to which the different frequencies, e.g., per rows "2" and "4," can be asynchronously presented and consistently detected. For the asynchronous operation, unique frequencies should be utilized between the left and right eye due to mixing that can occur in the subject that can affect classification.

While the example shown in FIG. 3C shows the frequencies being arranged in a certain order or increments, it is noted that the order of the sequencing of the unique frequencies can be varied (and still provide for similar performance).

In conjunction with a deep-learning algorithm and soft electronics hardware described herein, the EEG BMI system 100b can provide real-time data processing and classification, e.g., for 33 classes of SSVEP inputs. In a study reported herein, it was observed that the EEG BMI system 100b could provide for 33 identifiable classes with an accuracy of 78.93% within a 0.8-second acquisition window and 91.73% within a 2-second acquisition window.

Referring still to FIG. 3A, the SSE system 110b may also include an array of integrated stretchable interconnectors bonded to flexible microneedle electrodes (FMNEs) 104'. The soft-scalp-electronic system 110b may be fabricated using a flexible membrane circuit to have great mechanical compliance. The flexible membrane circuit can be integrated with electronic chips (e.g., front-end acquisition IC and network interface IC) and encapsulated to maintain mechanical compliance.

Each of the arrays of FMNEs 104', in the example shown in FIG. 3A, includes a set of high-aspect-ratio needles, e.g., greater than 2 (e.g., 800 μm in height with a base width of 350 μm). Other needle base to height ratios may be employed, e.g., 1, 1.1, 1.2, 1.3, 1.4, 1.5, 1.6, 1.7, 1.8, 1.9, 2.0. In some embodiments, the needle base to height ratios can be greater than 2.

The soft-scalp-electronic system 110b, in the example shown in FIG. 3A, is connected to arrays of FMNEs 104' attached or affixed to a wearable head strap 206 (shown as 206').

The electrode arrays 104' are connected to ADC front-end circuitries (e.g., comprising ADCs 132) of the soft-scalp-electronic system 110b. The soft-scalp-electronic system 110b includes the network interface (e.g., 134) that can communicate the acquired EEC signals to a BMI control system (e.g., 112). In the example shown in FIG. 3A, the BMI control system 112a is configured to process sequences from the EEG recording machine learning classification algorithm (e.g., 114) to generate SSVEP classifications that can be used as control signals to control VR/AR targets in a VR/AR system environment.

To address the complexity of the stimuli and to maintain a high level of classification performance, machine learning operations can be performed on a per-session basis. FIG. 4B shows an example method 330 of operation to configure and re-configure the BMI control system (e.g., 112) during run-time operation.

In the example shown in FIG. 4B, Method 430 includes acquiring (432) the EEG signals, e.g., via the soft-scalp-electronic system 110b. The EEG signals may be acquired during a calibration operation. Multiple training trials may be performed to acquire sufficient data to the train a machine-learning model with minimal bias. The calibration operation may be performed prior to each session. Method 430 then includes transmitting (434) the acquired signals to a training system (e.g., cloud infrastructure). The training system can pre-process (436) the acquired signals via segmentation (438) (e.g., segmenting data in the range of 0.8 seconds and 2 seconds), filtering (440) (e.g., using a bi-directional 3rd order high-pass Butterworth filter with a corner frequency of 2.0 Hz), and rescaling operation (441) (e.g., linearly rescaling between a range of −0.5 and 0.5).

The training system may perform classification operation (438) by training variations of the Spatial-CNN model with hyperparameters adjustments (e.g., size of filters, number of filters, and number of convolution steps). The training system then determines (440) if performance is improved. If so, the training system then transmits (442) the model parameters to a run-time system (e.g., the BMI control system 112).

In some embodiments, the EEG BMI system 100b for SSVEP can be used in combination with the EEG BMI system 100a for MI.

Example Method of Operation

Figure 4A:
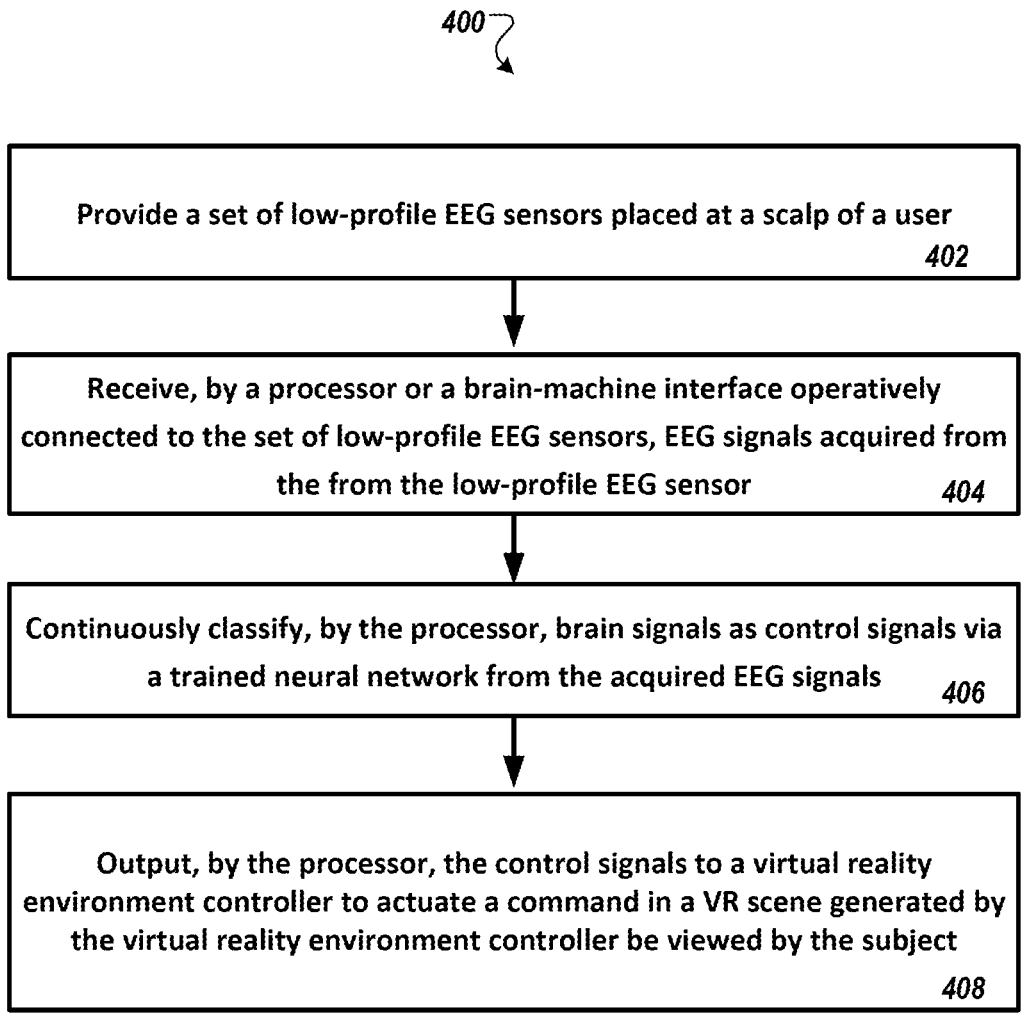
FIG. 4A illustrates a method of operating the example EEG brain-machine-interface system in accordance with an illustrative embodiment.
Figure 4B:
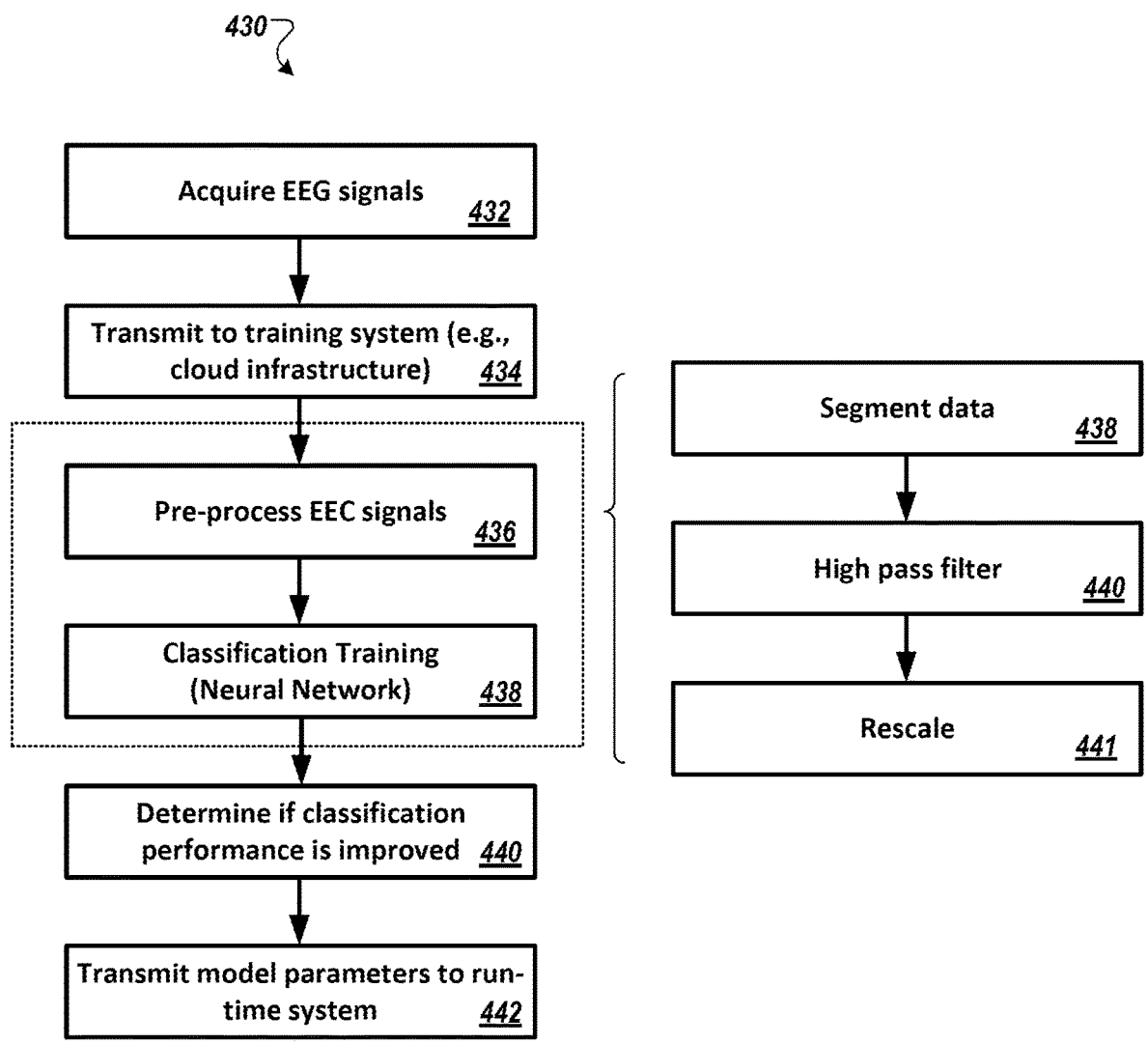
FIG. 4B shows an example method of operation to configure and re-configure the example EEG brain-machine-interface system during run-time operation in accordance with an illustrative embodiment.

FIG. 4A illustrates a method 400 of operating using an embodiment of the systems disclosed herein to output control signals. Method 400 includes (402) providing a low-profile EEG sensor, e.g., a described in relation to FIG. 1, 2A, 3A, or other BMI configurations described herein.

Method 400 then includes receiving (404) by a processor or a brain-machine interface operatively connected to the set of low-profile EEG sensors, EEG signals acquired from the low-profile EEG sensor receiving. Examples of the data acquisition are provided in relation to FIGS. 1, 2A, and 3A.

Method 400 then includes continuously classifying (406) by the processor brain signals as control signals via a trained neural network from the acquired EEG signals.

Method 400 then includes outputting (408) by the processor the control signals to a virtual reality environment controller to actuate a command in a VR scene generated by the virtual reality environment controller be viewed by the subject.

Example #1 Method of Fabrication of Flexible Microneedle Array

Figure 5A:
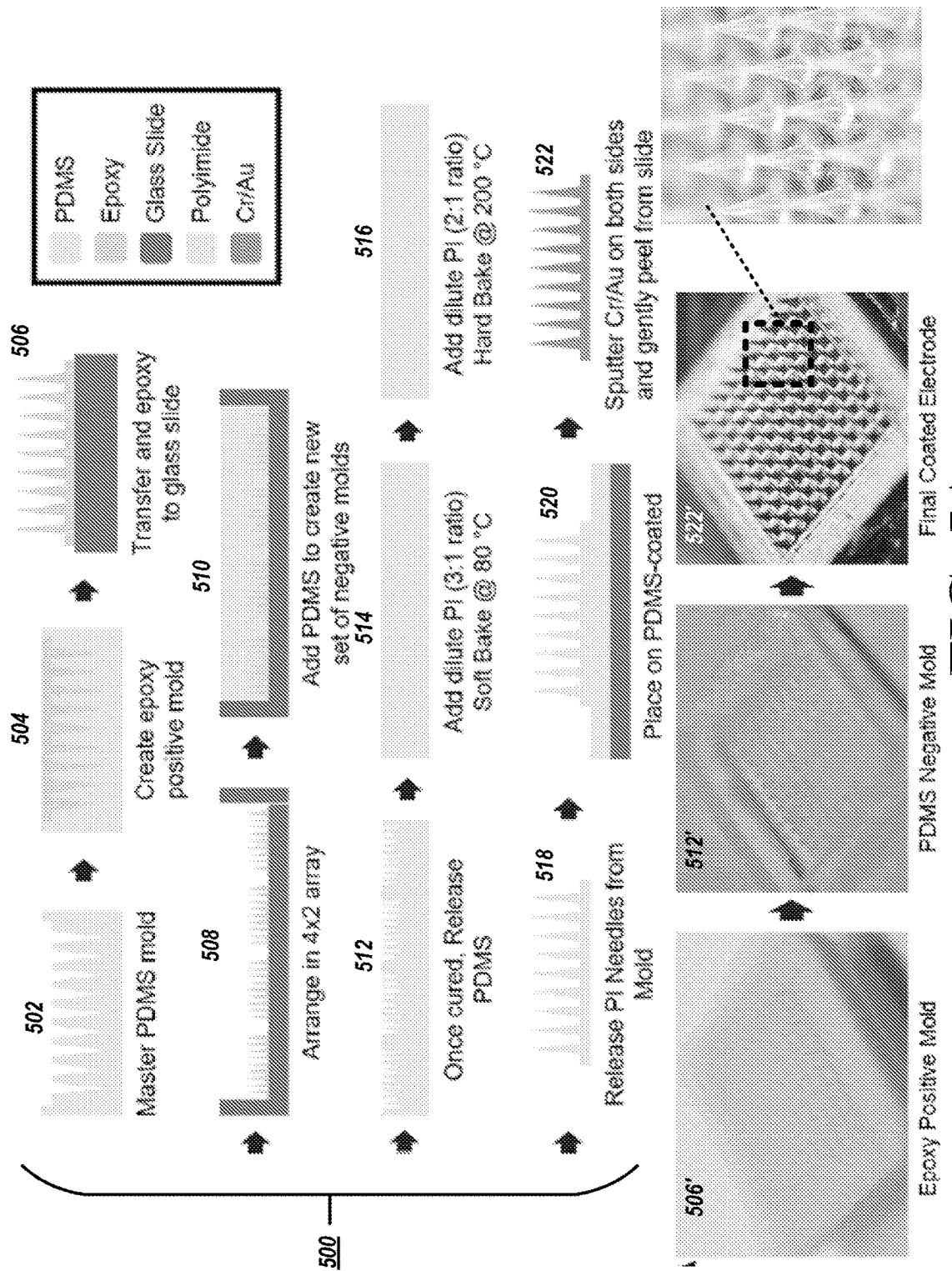
FIGS. 5A, 5B, 5C, 5D, and 5E each illustrates example methods of fabricating components of the example EEG brain-machine-interface system in accordance with illustrative embodiments.

FIG. 5A illustrates a method 500 of fabricating an array of electrodes on a substrate according to an example embodiment of the present disclosure. In the example of FIG. 5A, the area of each electrode array can be about 36 mm$^2$, which can improve the EEG spatial resolution over the conventional, large cup electrodes (100 mm$^2$) that typically require conductive gels. Other array size can be employed, e.g., about 10 mm$^2$, about 15 mm$^2$, about 20 mm$^2$, about 25 mm$^2$, about 30 mm$^2$, about 35 mm$^2$, about 40 mm$^2$, about 45 mm$^2$, about 50 mm$^2$ in which "about" refers to range of +1 mm, +2 mm, or +2.5 mm. In some embodiments, the array size can be between than 50 mm$^2$ and 100 mm$^2$. Typical EEG with conductive gels is about 100 mm$^2$ in size.

In FIG. 5A, Process 500 includes providing (502) a master negative PDMS (Polydimethylsiloxane) array mold. The PDMS array mold can be cleaned using IPA and dried at 60° C. for 10 minutes. Process 500 includes creating (504) an epoxy positive mold using the negative PDMS mold. The positive mold can be formed by an epoxy resin (e.g., the resin EpoxAcast manufactured by Smooth On, Inc). Process 500 includes transferring (506) the epoxy positive mold to a glass slide. An adhesive can be used to bond the PDMS negative mold onto the glass slide as a bonding layer of PDMS. Image 506' shows a positive epoxy mold. Process 502 to 506 can be repeated to form additional copies of the epoxy positive mold. In some embodiments, the PDMS negative mold can be treated with ambient air plasma (e.g., for 2 minutes).

Process 500 includes positioning (508) the copies of the epoxy positive mold in an array inside a tray. Process 500 includes adding (510) additional PDMS to the tray to form a new set of negative molds. The mold illustrated in step 508 is a 4×2 array, but it should be understood that any number of epoxy molds created in steps 502 to 506 can be used. Process 500 includes releasing (512) the PDMS negative mold from the tray used in steps 508 and 510. Image 512' shows a negative silicone mold formed from PDMS. Image 522' shows the final coated electrode. The mold components are formed in steps 502 thru 512.

To fabricate the needles, the Process 500 first includes adding (514) a dilute polyimide (PI) solution to the PDMS negative mold and then can be soft-baked (e.g., at 80° C. for 10 minutes). Process 500 includes adding (516) a second dilute polyimide solution to the mold of 516, which can then be hard-baked (e.g., at 200° C. for 1 hr.) In the example illustrated in FIG. 5A, the first dilute polyimide solution is a 3:1 ratio solution, and the second dilute polyimide solution is a 2:1 solution. Other ratios and processing times can be used. Process 500 includes removing (518) the PI needles from the mold, e.g., peeling the polyimide microneedle array (PI MNA) from the PDMS mold.

The PI needles can then be coated with a conductive layer. Process 500 may include placing (520) the PDMS needles on a PDMS coated slide. A thin layer of Polyimide (PI) (e.g., PI sold under the trademark PI 2610 by HD Microsystems) can be applied to the negative PDMS mold by scraping with a razor blade before the soft bake. The PI can be spin-coated on the mold, e.g., at 800 RPM for 60 seconds. Process 500 then includes coating (522) the PI needles using sputter deposition, e.g., via Cr coating and then Au coating where the depths of CR and AU are 5 nm and 200 nm, respectively. The sputtering can be performed in multiple steps. For example, the top or bottom surface of the PI needles can be sputter coated in one step, and then the remaining surface can be sputter coated in the next step.

Example #2 Method of Fabrication of Flexible Microneedle Array

Figure 5B:
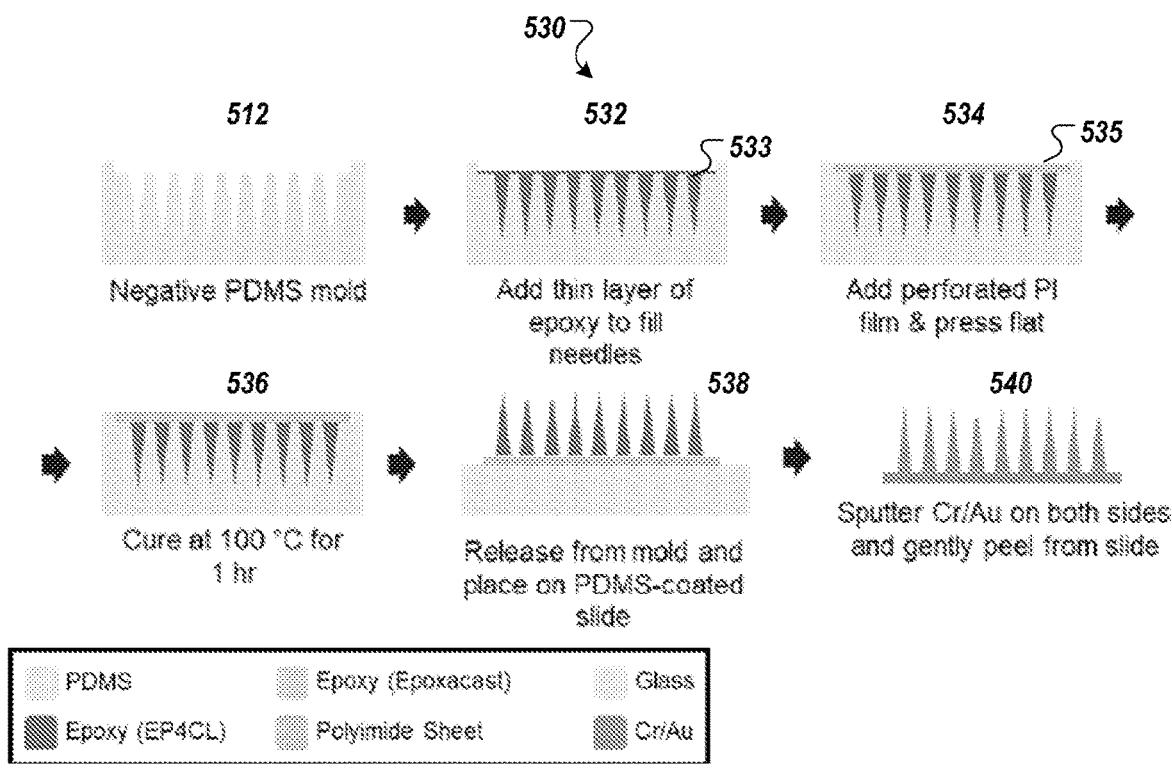
Figure 5B:
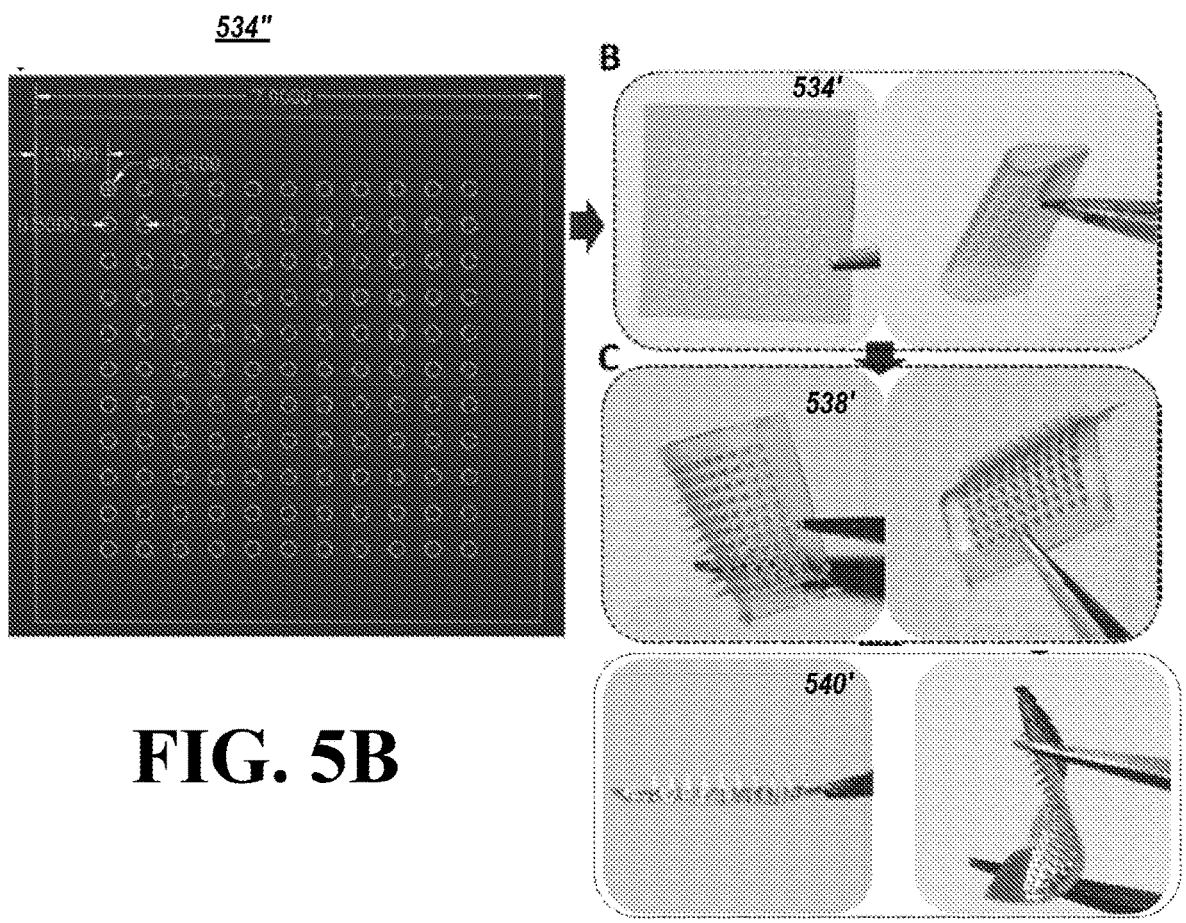

FIG. 5B illustrates another method 530 of fabricating an array of electrodes on a substrate according to an example embodiment of the present disclosure. Method 530 includes creating a PDMS negative mold (512), e.g., as described in relation to FIG. 5A. Process 530 then further includes adding (532) a thin layer of epoxy (e.g., EP4CL-80MED, Master Bond Inc.) to form the needles 533. The epoxy can be one-part epoxy with high tensile and compression strength, as well as its biocompatibility. One part epoxy can be used without a solvent, which can prevent the epoxy from bubbling and does not require a mixing step, avoiding air being mixed into the epoxy by mixing. Process 530 then includes adding (534) a perforated polyimide sheet (535) to the needles. Image 534" shows an example design of the perforated polyimide sheet, and images 534' shows an example perforated polyimide sheet that is fabricated, which has high compliance and flexibility. Process 530 then includes performing a low-temperature cure (536) (e.g., 100° C. for 1 hour). Low-temperature curing can be employed to allow the molds to repeated used over more replica molding cycles. In contrast, in some embodiments, a high-temperature PI cure can destroy the PDMS molds in as few as three fabrication cycles.

Process 530 then includes releasing (538) the needle structure from the mold and placing it on a PDMS-coated slide. The needle can be coated (540) by sputtering Cr/AU on both sides of the needle structure. Image 538' shows the needle assembly prior to Cr/AU coating, and image 540' shows the needle assembly after the Cr/AU coating.

Example Method of Fabrication of the Flexible Main Circuit

Figure 5C:
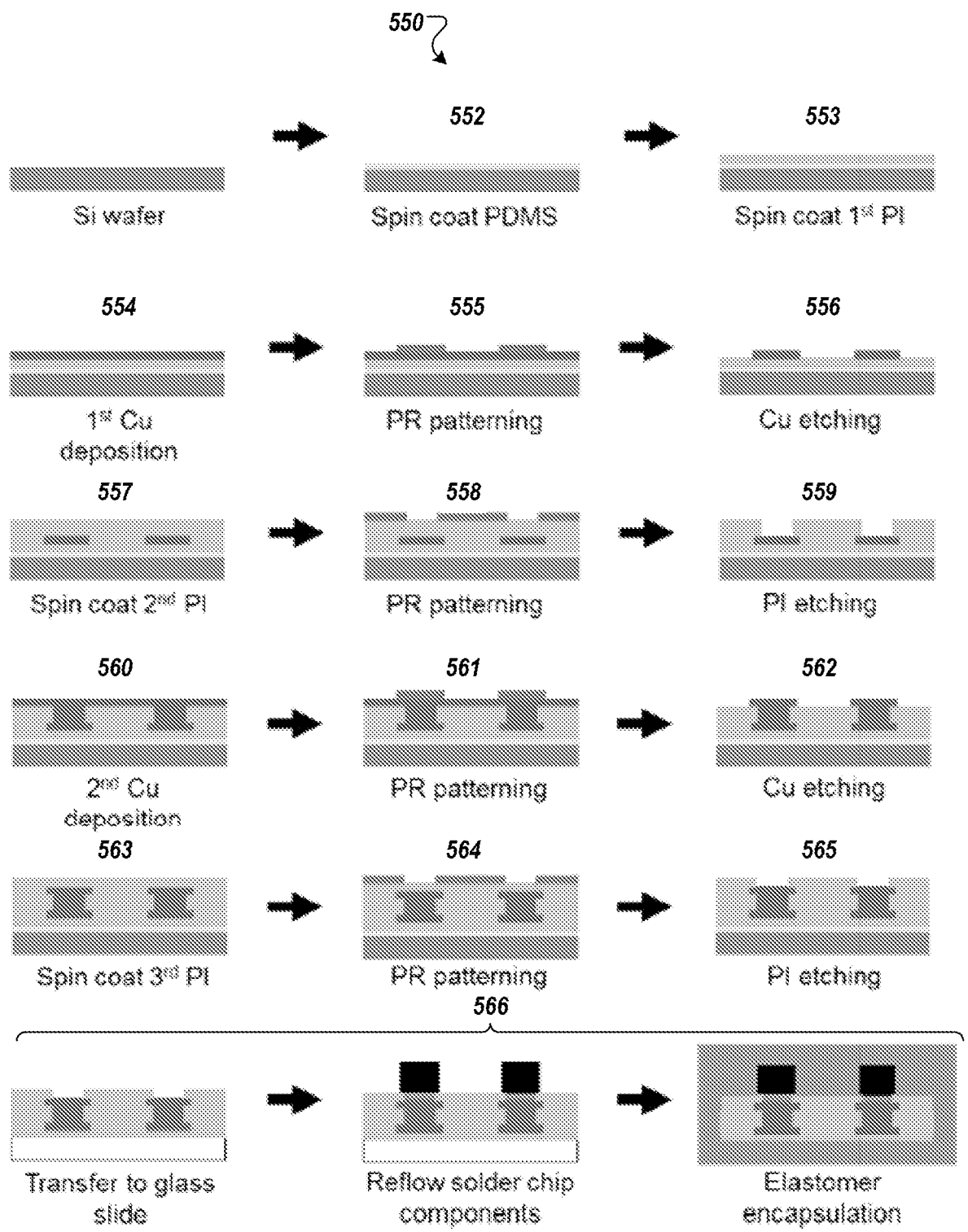
Figure 5D:
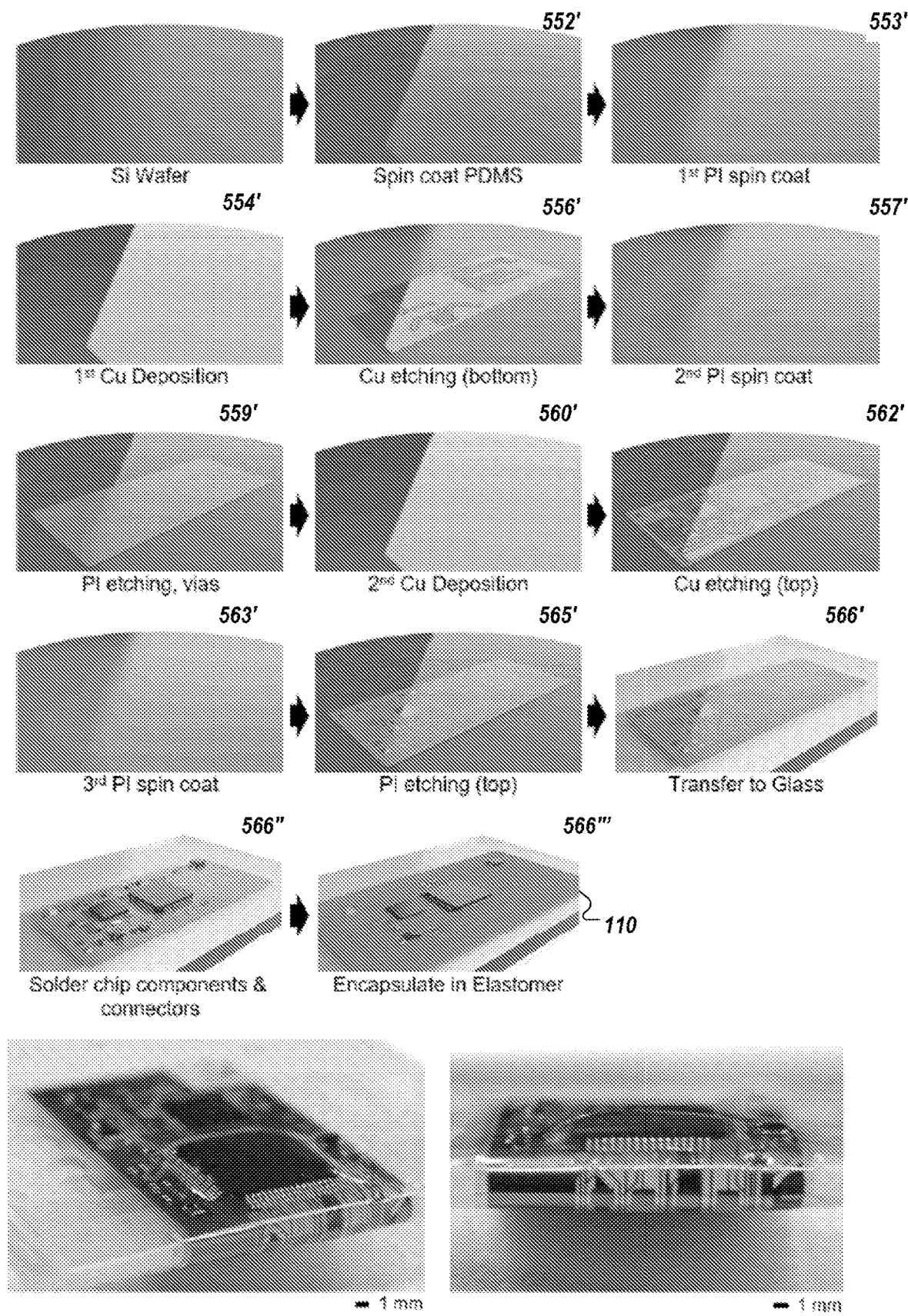

FIGS. 5C and 5D illustrate a method 550 of fabricating an example flexible main circuit in accordance with an illustrative embodiment. The flexible main circuit can include a polyimide substrate that can be sufficiently thin to allow electrode flexion to conform to the scalp surface.

Method 550 includes spin coating (552) the PDMS on a cleaned silicon wafer (e.g., at 3000 rpm for 30 sec). The PDMS-coated wafer can be cured (e.g., on a 150° C. hot plate for 5 min). Oxygen plasma treatment can be performed to render the PDMS hydrophilic. Image 552' shows the spin-coated PDMS. Method 550 then includes spin coating (553) polyimide (e.g., at 4000 rpm for 1 min) and bake in a vacuum oven (e.g., at 250° C. for 3 hr, including ramping steps). Image 553' shows the first polyimide spin-coated wafer.

Method 550 then includes sputtering (554) copper (e.g., 500 nm copper) for the 1 st metal layer. Image 554' shows the first copper deposited wafer.

Method 550 then includes patterning (555) the wafer by spin coating photoresist (e.g., SC1827) (e.g., at 3000 rpm for 30 sec) and baking it (e.g., on a 110° C. hot plate for 1 min); exposing UV with the 1st metal pattern (ground) using a mask aligner (e.g., MA6); and developing the exposed photoresist with a developer (e.g., MF-319).

Method 550 then includes etching (556) the exposed copper with a copper etchant (APS-100, diluted 1:1 with DI water) and strip photoresist. Image 556' shows the bottom Cu etched circuit with the Cu etching performed thereon. Method 550 then includes spin coating (557) polyimide (e.g., at 850 rpm for 1 min) and baking it in a vacuum oven (e.g., at 250° C. for 3 hr, including ramping steps). Image 557' shows the second polyimide spin-coated wafer.

Method 550 then includes patterning (558) the wafer by spin coating photoresist (e.g., AZP4620) (e.g., at 1000 rpm for 30 sec) and baking it (e.g., on a 95° C. hot plate for 4 min); developing the exposed photoresist with a developer (e.g., AZ400K, diluted with 4 parts of DI water). Method 550 then includes exposing (559) the PI to an oxygen plasma etch using reactive ion etching (Plasma-Therm) and removing the photoresist. Image 559' shows the polyimide circuit etched with vias.

Method 550 then includes depositing (560) a second Cu layer by sputtering (e.g., 1.5 μm copper for the 2nd metal layer). Image 560' shows the 2nd deposition wafer.

Method 550 then includes patterning (561) the wafer by spin coating photoresist (e.g., AZP462), e.g., at 3000 rpm for 30 sec, and baking it (e.g., on a 95° C. hot plate for 4 min); exposing UV with the 2nd metal pattern using a mask aligner (e.g., MA6); and developing the exposed photoresist with a developer (e.g., AZ400K, diluted with 4 parts of DI water). Method 550 then includes etching (562) exposed copper with a copper etchant (APS-100, diluted 1:1 with DI water) and them removing the photoresist. Image 562' shows the top Cu etched circuit.

Method 550 then includes spin coating (563) polyimide (e.g., at 4000 rpm for 1 min) and bake in a vacuum oven (e.g., at 250° C. for 3 hr, including ramping steps). Image 563' shows the third polyimide spin-coated wafer.

Method 550 then includes patterning (564) the wafer by spin coating photoresist (AZP462), e.g., at 2000 rpm for 30 sec, and baking it (e.g., on a 95° C. hot plate for 4 min); developing the exposed photoresist with a developer (AZ400K, diluted with 4 parts of DI water). Method 550 then includes performing (565) oxygen plasma etch exposed PI using reactive ion etching (Plasma-Therm) and stripping the photoresist to produce the final flexible circuit. Image 565' shows the polyimide etched top circuit with the exposed Cu deposited layer.

Method 550 then includes installing (566) ICs on the flexible circuit by transferring the circuit to a glass slide (see images 566'); reflowing solder onto chip components to install the ICs (see image 566"); and encapsulating the full circuit (e.g., 110) in an elastomer (see image 566'''). FIG. 5D shows the final fabricated flexible circuit, which is bent over a glass slide. Description of alternative methods are described in Mahmood et al. 2021; Mahmood et al. 2019; Zavanelli et al. 2021.

Example #1 Method of Fabrication of the Stretchable Interconnects

Figure 5E:
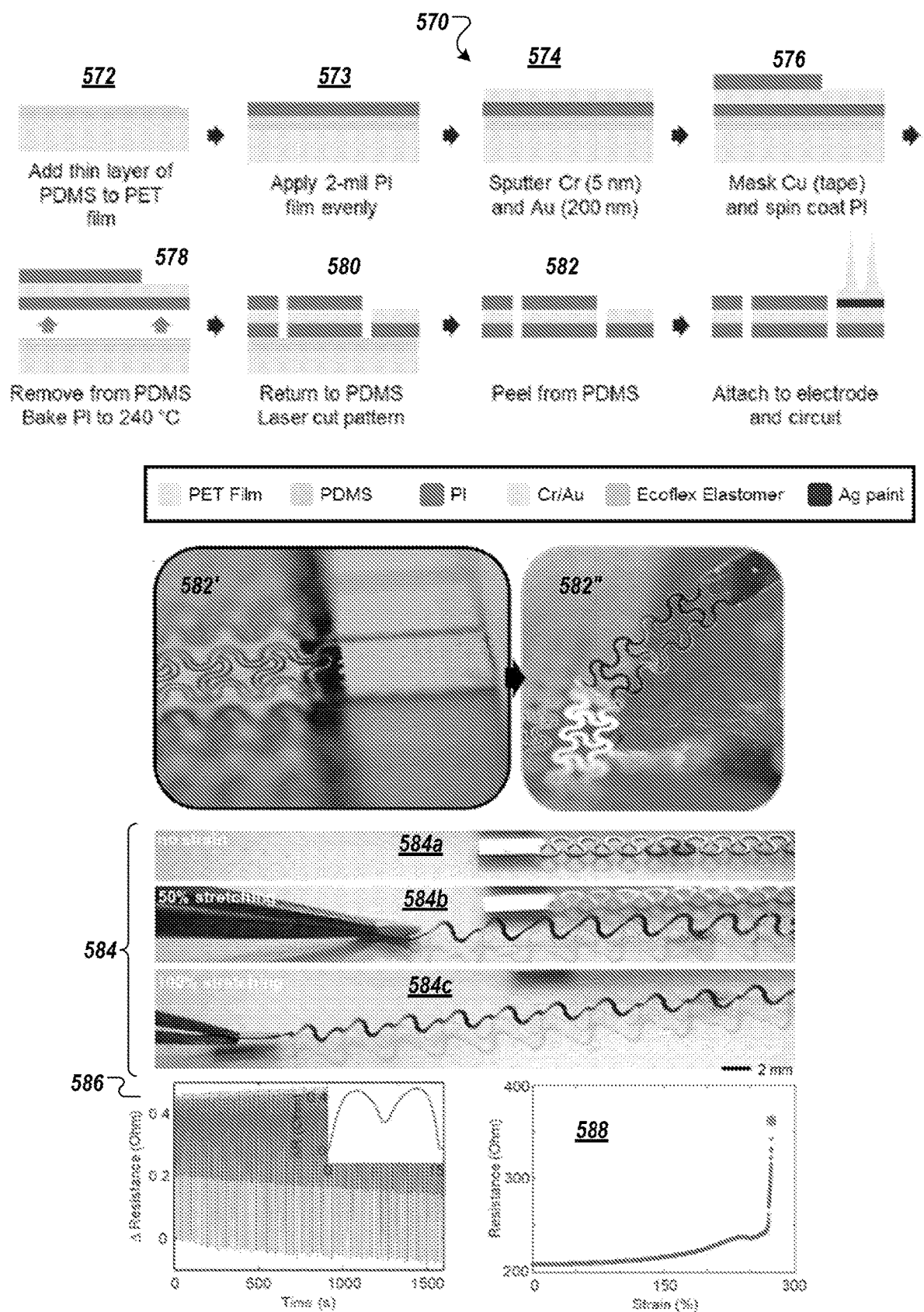

FIG. 5E illustrates a method 570 of fabricating an example flexible interconnect (e.g., 128) in accordance with an illustrative embodiment. To improve throughput and reduce fabrication code (e.g., as compared to conventional microfabrication in a cleanroom), Method 570 may employ a femtosecond laser cutter (WS-Flex USP, OPTEC) to fabricate the stretchable interconnect (e.g., 128) using a micro-machining process. Method 570 may include three main fabrication process (PET substrate preparation for polyimide film, sputtering Cr/Au on a polyimide film, and laser cut patterning).

To prepare the PET substrate for PI film, Method 570 may include spin-coating (572) PDMS (Sylgard 184, Dow Corning) onto the PET sheet (e.g., at 700 rpm for 60 seconds), curing it (e.g., at 70° C. for 30 min), and then applying the prepared Cr/Au on PI sheets onto the PDMS (e.g., ensuring that it has fully adhered and there are no bubbles or ripples). Method 570 may then include depositing (573) excess PI 2610 and spin-coating (e.g., at 3000 rpm for 1 minute), performing a first baking step on the hot plate (e.g., at 70° C. for 30 mins), and after first baking step, removing PI film from PDMS/PET substrate and taping (576) it directly to clean hot plate to prevent the curling and contraction from heat), then proceeding with a second baking operation (578) (e.g., at 100° C. for 15 min, then 150° C. for 15 min, then 200° C. for 15 min, then 250° C. for 15 minutes).

To sputter Cr/Au on PI film, Method 570 may first include taking a 0.5 mil sheet of PI film (Kapton HN Film, 0.5 mil, DuPont), cleaning it thoroughly, e.g., first with IPA, then with acetone, and drying after each cleaning. Method 570 may then include cutting the PI film into sheets of size 6 in×4 in to fit inside the sputter machine. Method 570 may then include sputtering (574) Cr/Au (10 nm/200 nm) on the PI film.

To pattern with a laser cutter (580), Method 570 includes reapplying the PI film sandwich onto the PDMS on PET substrate and using a femtosecond laser cutter (WS-Flex USP, OPTEC), secure the materials to the stage using a vacuum. Method 570 may then include preparing the material by aligning it with the stage and zeroing the laser head so that the masked areas align with the interconnect ends in the design. The pattern can be cut, e.g., by IFOV mode, 60 kHz pulse, 60 movement speed, 60 jump speed, 12% power, and 2 repetitions (3 passes total). Method 570 may then include peeling (582) (e.g., manually peeling) the final, cut interconnects from the PDMS substrate using a fine-tipped tweezer. Image 582' shows the patterned interconnectors prior to it being peeled. Image 584 shows the patterned interconnectors as it is being peeled. Images 584 show example stretchability characteristics of the flexible interconnect (e.g., 128) at 0%, 50%, and 100% stretching (584a, 584b, and 584c, respectively). Plot 586 shows a mechanical test result of the flexible interconnect (e.g., 128) over a set of cycles, and plot 588 shows a strain/resistance curve for the flexible interconnect (e.g., 128). The test shows the mechanical fracture after 250% of tensile stretching.

Example #2 Method of Fabrication of the Stretchable Interconnects

A substrate for the interconnector is prepared by an electron-beam evaporating Cr/Au (5 nm/200 nm) on a 2-mil PI film (200HPP-ST, DuPont). The metal-coated PI film can then be laminated on a PDMS-coated PET film to hold the material during the laser cutting process. Once an array of stretchable interconnectors has been patterned on the metal-coated PI film, excess materials other than the patterned interconnectors can be manually peeled off from the PDMS-coated PET film. With water-soluble tape, the interconnectors are transfer-printed on a soft elastomer substrate (Ecoflex 00-30, Smooth-On, Inc.), and areas other than their contact pads are encapsulated with an additional layer of elastomer. The interconnectors are electrically connected to the electrode and sensor with silver paint (Fast Drying Silver Paint, Ted Pella).

Experimental Results and Examples #1

Two studies were conducted to develop and evaluate a virtual reality brain-machine interface: the first study employed motor imagery BMI and the second study employed steady-state visually evoked potentials (SSVEP).

Figure 6A:
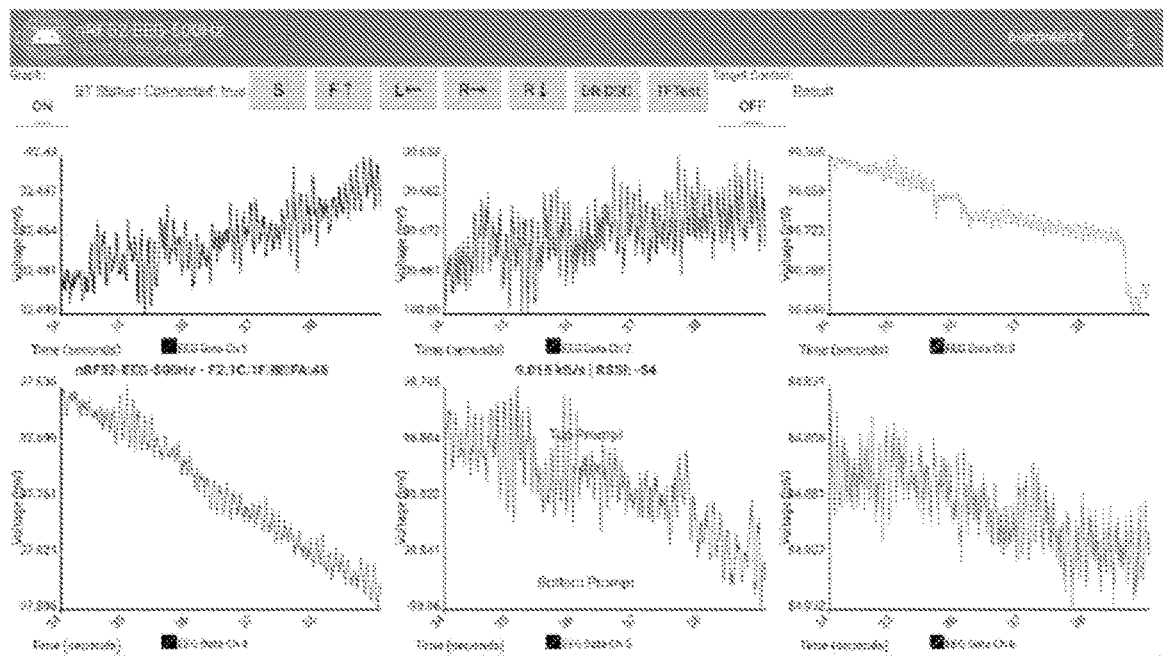
FIGS. 6A, 6B, 6C, 6D, and 6E each shows aspects of a study to develop virtual reality (VR) implementation for motor imagery training and real-time control using the example EEG brain-machine-interface system in accordance with an illustrative embodiment.

Motor Imagery Study Overview. FIGS. 6A, 6B, 6C, 6D, and 6E each shows aspects of a study to develop virtual reality (VR) implementation for motor imagery training and real-time control using the example EEG brain-machine-interface system in accordance with an illustrative embodiment. Specifically, FIG. 6A illustrates an overview of the study to develop a virtual reality (VR) implementation for motor imagery training and real-time control of a video game demonstration. The study evaluated a fully portable, wireless, soft scalp electronics that includes at least three major components: 1) multiple flexible microneedle electrodes for mounting on the hairy scalp, 2) laser-machined stretchable and flexible interconnects, and 3) a low-profile, flexible circuit. The study also included a virtual reality (VR) component that can allow for a convenient and immersive training environment to assist with motor visualization. These components were used in the study as a monolithic EEG system optimized for minimizing motion artifacts and maximizing signal quality. Epidermis-penetrating electrodes were employed to provide optimal impedance density on the scalp, improve the signal-to-noise ratio, and improve spatial resolution for MI recording. Overall, the study showed that embodiments of the exemplary devices and systems provide a feasible approach to a high-performance BMI system that can operate well with a powerful machine-learning algorithm and in a virtual reality environment. Additionally, the study showed that embodiments of the present disclosure can employ imperceptible, hair-wearable systems with only 6 EEG channels and can achieve high accuracy of 93.22±1.33% for four classes with a peak information transfer rate of 23.02 bits/min with four human subjects.

Methodology. The study developed a customized Android application configured to provide real-time, continuous motor imagery classification of 6 channels of MI signals. The Android application was used to evaluate the training and testing processes of a VR. In the training system, the system presented modified views (630) of VR visuals to a subject with text and animation prompts that are designed for MI response testing. In the example shown in FIG. 6A,
VR screen 632 is an example VR scene comprising disembodied hands and feet. VR screen 633 is an example VR scene that includes clear color-coded visual cues and text prompt that can be actuated by the user through motor imagery. The developed application showed the VR scene 635 along with the associated EEG signals 637 that were observed by the measurement equipment. Plots 619 show the acquired EEG signals 637 from one of the interfaces of the Android application.

The results of the example embodiment of the present disclosure demonstrate the superior performance of the VR environment as a training implement (2240 samples from 4 subjects, 560 samples per subject, window length w=4 s). Additional accuracy improvement was also observed with the FMNE and VR setup. The enhanced accuracy may be attributed to the immersive VR training program with disembodied hands and feet shown (632) within the subject's field of view in approximately the same position as their existing limbs. In the study, the subject could gently rotate or tilt their head and visualize their hands or feet in the VR application.

Figure 6B:
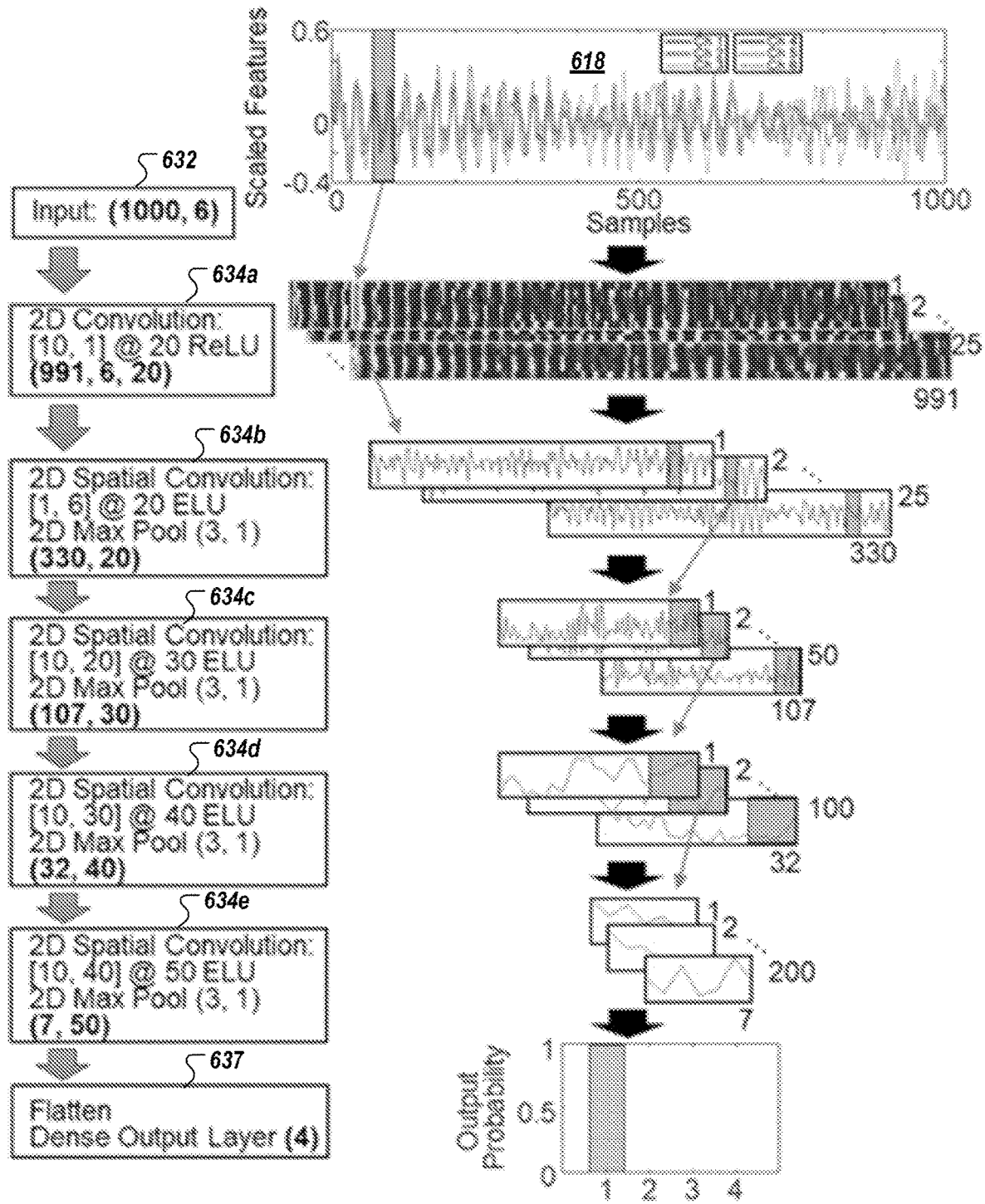

Neural Network Training. FIG. 6B shows the neural network training of the MI classification system used in the study. In the example shown in FIG. 6B, training for a spatial convolutional neural network for motor imagery classification is shown. The system acquired six EEG channels (618) and decomposed them into spatial features from multiple dipolar sources of the motor cortex. The input (618) included six EEG data having a pre-defined sample size (shown in this sample as 1000 samples). The spatial convolutional neural network employed in the study included a number of hidden layers (634) (shown as "2D convolution" 634a and "2D Spatial Convolution" 634b, 634c, 634d, 634e). At step 637, a flatten step can be performed to generate a dense output layer.

Figure 6C:
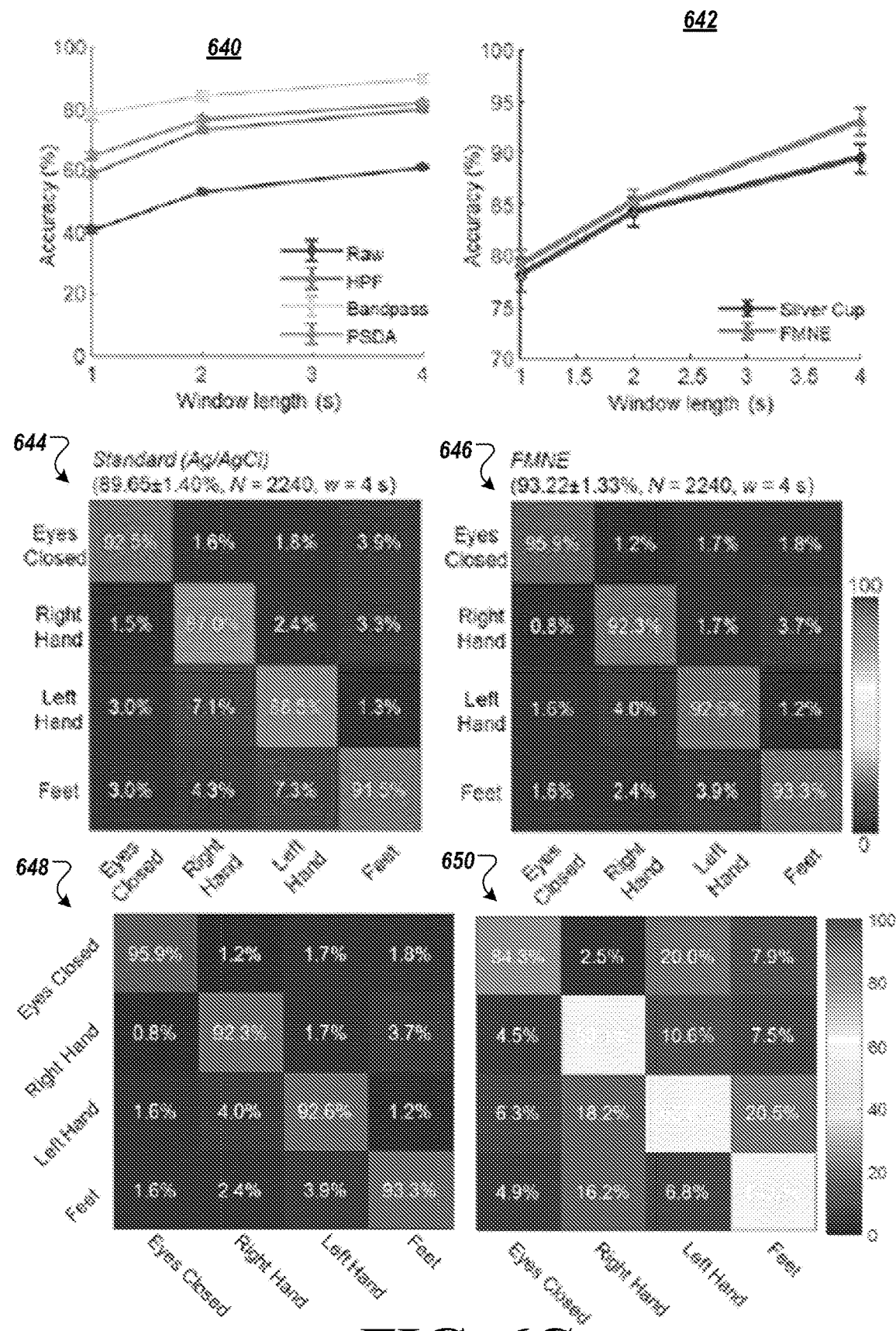

Classification Results. FIG. 6C illustrates classification results (N=4 subjects) using the spatial CNN of FIG. 6B in the study. FIG. 6C includes a comparison plot 640 of spatial-CNN classification accuracy among four analysis bases, including raw data, high-pass filtered data (HPF), band-pass filtered data (Bandpass), and power spectral density analysis (PSDA). The analysis was conducted and is presented over multiple window lengths (1, 2, and 4 seconds). The error bars show a standard error from four subjects.

FIG. 6C also includes a second comparison plot 642 of spatial-CNN classification accuracy between using conventional Ag/AgCl gel electrodes and the exemplary FMNE. The analysis was also conducted across multiple window lengths (1, 2, and 4 seconds), and the error bars show a standard error from four subjects.

FIG. 6C also illustrates two confusion matrices (644, 646), indicating results from a real-time accuracy test of motor image brain data acquired by conventional Ag/AgCl electrodes and by the exemplary FMNE. In matrix 644, the results for conventional Ag/AgCl electrodes shows an overall accuracy of 89.65% (N=2,240 samples, window length=4 seconds, and 4 human subjects). In matrix 646, the results for the exemplary FMNE show an overall accuracy of 93.22% (N=2,240 samples, window length=4 seconds, and 4 human subjects).

FIG. 6C also illustrates two additional confusion matrices (648, 650) indicating results from a real-time accuracy test of motor image brain data, acquired using Spatial-CNN classifier and using a standard-CNN classifier. In matrix 648, the results for the Spatial-CNN classifier performance show an overall accuracy of 93.3% on the FMNE dataset (n=2240 samples from 4 subjects, 560 samples per subject, window length w=4 s). In matrix 650, the results for the standard-CNN classifier performance on the FMNE dataset show an overall accuracy of 64% (n=2240 samples from 4 subjects, 560 samples per subject, window length w'=4 s).

Figure 6D:
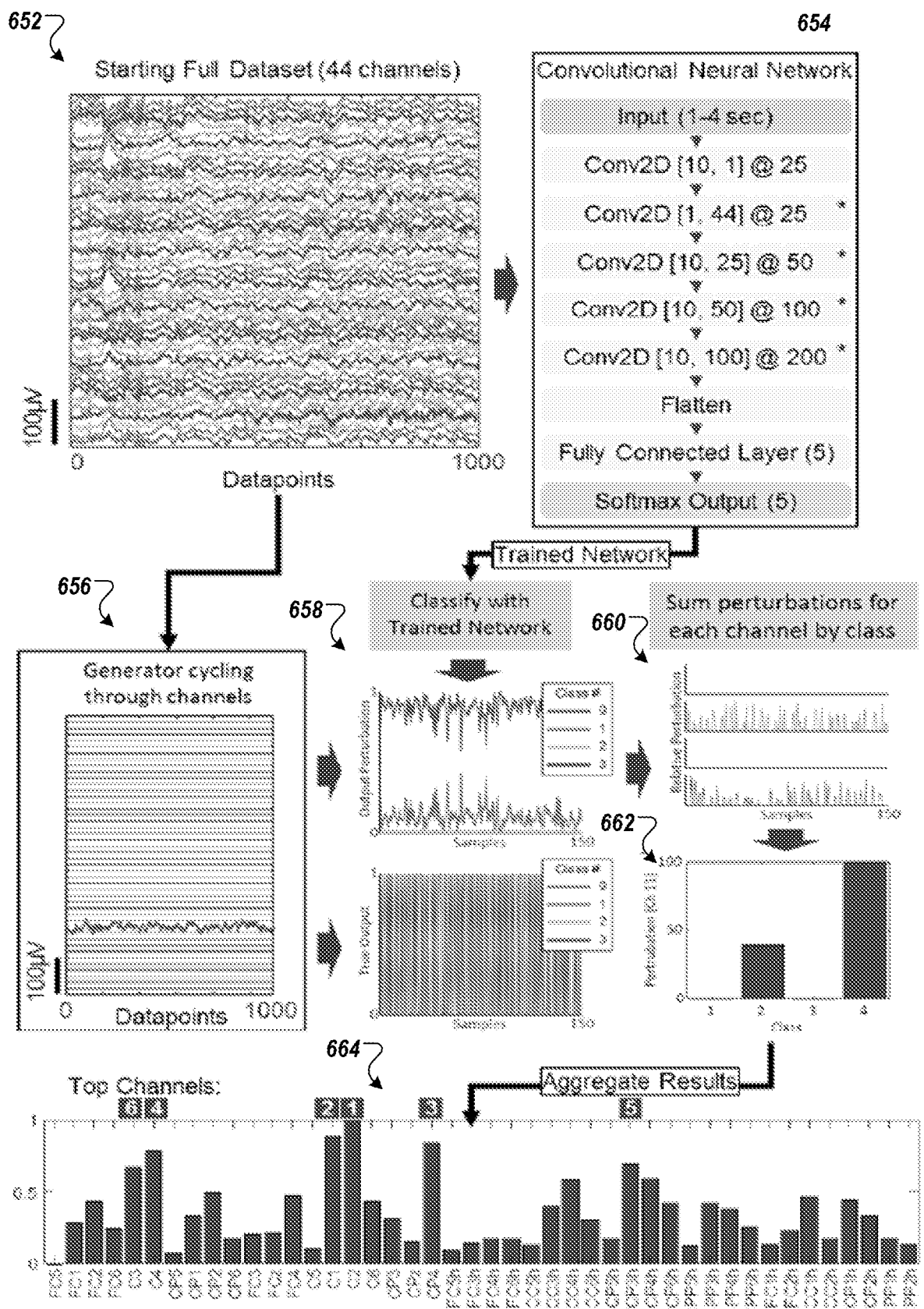
Figure 6E:
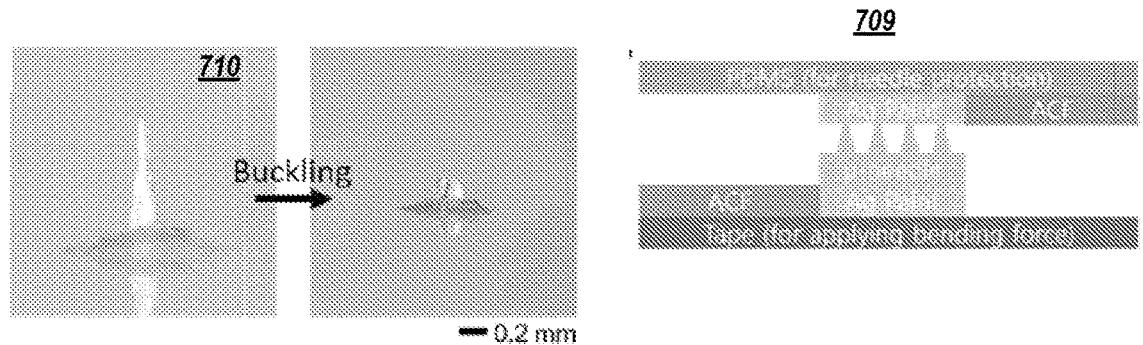

FIG. 6E illustrates a table showing the comparison of the example embodiment to other devices as reported in the literature [15, 20, 25, 26, 27, 21]. Indeed, it can be observed that exemplary BMI sensor device and system can provide the accurate control, e.g., for a virtual reality game using a MI paradigm. In the table, it is shown that the exemplary BMI sensor device and system, in an implementation, can provide 93%+ accuracy to provide an ITR of about 23 bits/minute using only 6 electrodes. Other performance results for other configurations are also reported herein.

Channel Selection Analysis. FIG. 6D shows the results of a preliminary analysis performed in the study to evaluate the optimized numbers of channels and their selection. 44-channels data out of conventional 128 channels from 13 healthy and normal subjects were considered for the analysis, as performed in a prior work (High-Gamma Dataset) [1]. The analysis determined 6 optimal channels from the 44 channels that were the most meaningful. The 6 channels were then implemented as the sensory array set, e.g., as shown and described in relation to FIG. 2. Other channels maybe similarly selected depending on the patient or subject that is evaluated, including those that are symptomatic.

In the example shown in FIG. 6D, the full dataset (652) employed in the study is shown. The data were preprocessed using a 3rd-order Butterworth bandpass filter, with corner frequencies at 4 Hz and 30 Hz, and split into windows of 4 seconds.

The data were used to train (654) a convolutional neural network (CNN) with standard convolutions on the first layer, with a filter size of (10, 1), followed by four spatial convolutional layers, to generate a trained network.

The data (652) were also evaluated (656) using a generator that cycled through the data channels (while eliminating the remaining channels) to calculate the output perturbation on the selected channels. This resulting data was fed into the trained network (generated from 654). The output perturbations are compared with the true expected outputs to generate (658) the relative perturbations for that channel. These relative perturbations are summed (662) over the classes to generate a final perturbation value for each of the channels.

The results are then compared and ranked (664). The bar chart shows each channel's relative perturbations with the top-6 channels labeled. The instant study employed a reduced number of electrodes (i.e., 6), which also reduced the complexity of the setup without significantly reducing classification performance.

Indeed, for the analysis, it was observed that a smaller number of channels than the conventional EEG setup may be employed using the exemplary FMNEs. The approximate positions of the electrodes corresponding with the standard 10-10 electrode placement system are discussed in [16].

Figure 7A:
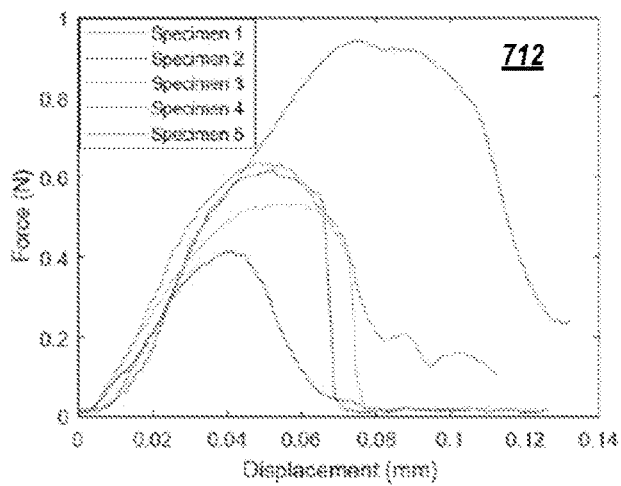
FIGS. 7A and 7B shows mechanical characterization results of components of the example EEG brain-machine-interface system in accordance with illustrative embodiments.

Buckling Force Evaluation of Microneedle Electrode. FIG. 7A shows the results from a quantitative mechanical test conducted during the study for the buckling force performance of the exemplary microneedle electrode, e.g., fabricated using processes described in relation to FIG. 5B. Specifically, FIG. 7A shows SEM observations (710) of microneedle electrodes evaluated under a motorized force gauge applied via an axial force upon a single microneedle. Plot (712) shows the force versus displacement curve from buckling force evaluation for five electrodes. It was observed that the five fabricated FMNEs could withstand an averaged applied force up to at least 626 mN, which is well above the skin insertion force (20-167 mN) of a single microneedle [17].

Figure 7B:
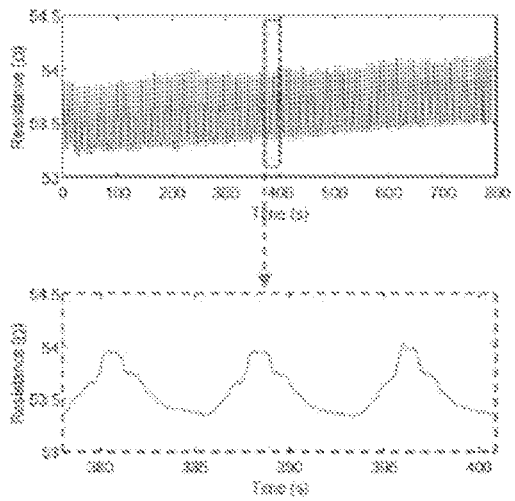

Flexibility evaluation of a microneedle electrode. FIG. 7B shows results from a cycle bending mechanical test to evaluate the flexibility of the exemplary FMNEs, e.g., to evaluate mechanical robustness in tissue insertion. The exemplary FMNE were configured as gold-based electrodes to be mounted on the skin surface, which are safe to use due to their excellent biocompatibility. Diagram 709 shows a schematic of the cross-section of the test specimen. During the test, needle electrodes were continuously bent up to 100 times with a radius of curvature of 5 mm while the change of electrical resistance was measured. The result shows a negligible resistance shift of less than 0.6Ω.

Impedance Density Characterization of Microneedle. Table 1 shows the results of a comparison study of impedance and impedance density of microneedle (MN) electrodes. In the study, different microneedle designs of varying heights were evaluated. The design included a fixed base width of 200 μm and a pitch of 500 μm in a 14×14 array.

TABLE 1

| Electrode | 500 μm MN | 600 μm MN | 700 μm MN | 800 μm MN | MVAP (Ag/AgCl) electrode | Flat gold film electrode |
|---|---|---|---|---|---|---|
| Area (mm$^2$) | 49 | 49 | 49 | 49 | 96 | 49 |
| Impedance (kΩ) | 43.6 | 35.7 | 29.7 | 23.3 | 20.8 | 129.3 |
| Impedance Density (kΩ·cm$^2$) | 21.4 | 17.5 | 14.6 | 11.4 | 20.0 | 63.4 |

Impedance density (ID; kΩ·cm2) can be calculated using the measured impedance (Z; kΩ) multiplied by the measured electrode contact area (A; cm2): ID=Z*A.

Motor Imagery Discussion. Brain-machine interfaces (BMIs) offer a possible solution for individuals with a physical disability such as paralysis or brain injury resulting in similar motor dysfunction. Among them, a significantly challenging disorder is a locked-in syndrome, where an individual is conscious but unable to move or communicate [1]. Here, BMIs may be able to restore some function to these individuals, providing a greater capability for movement and communication, and improving quality of life [1, 2]. Electroencephalography (EEG) is the premier non-invasive method for acquiring brain electrical activity [3-5], where electrodes mounted on the scalp surface record the sum of post-synaptic potentials in the superficial cortex. Conventional research- and medical-grade EEG use a hair cap or a large headgear with multiple rigid electrodes to measure signals at the scalp. These heavy and bulky systems are uncomfortable to wear and often require large, rigid electronics either attached to the system or separated using long lead wires [3]. These devices depend heavily on consistent skin-electrode impedances and typically suffer from significant motion artifacts and electromagnetic interferences [3, 4]. Typically, electrodes are coupled with conductive gels or pastes to improve surface contact and reduce impedance. These interfacial materials are a source of noise due to changes in impedances at these locations due to motion artifacts or material degradation. Overall, conventional systems require extensive setup times and are inconvenient and uncomfortable to use.

Improved signal acquisition can be performed through the use of lightweight, flexible electronics and dry electrodes [6, 6', 6"]. The latest EEG designs display a trend toward wireless, wearable EEG. These can be preferable for day-to-day mobile EEG monitoring, with compact, battery-powered designs over conventional amplifiers and hair-cap EEG. For mobile systems, dry electrodes are preferred due to short setup times, no skin irritation, and excellent long-term performance [7, 8]. In addition, they often perform better than gel-based EEG sensors while providing long-term wearability without reduced signal quality [4, 7, 9]. Recent developments in skin-interfaced electrodes for biopotential acquisition demonstrate new strategies and solutions for on-skin bioelectronics [10]. Examples include the use of screen-printed highly conductive composites [11] and nanowire-based networks fabricated via interfacial hydrogen bonding in solution [12] with excellent stretchability and interfacial conductive properties. There is a multitude of strategies for non-invasive EEG BMI paradigms [13]. Steady-state visually evoked potentials (SSVEPs) can be studied [3], where subjects can operate a machine interface by shifting their gaze between flickering stimuli of differing frequencies. However, with the recording of SSVEPs, practical applications are limited due to the requirement of an array of visual stimuli impeding the operator's view. Also, the bright, flickering stimuli can cause eye strain and fatigue when used for extended periods. Alternatively, motor imagery (MI) is a greatly advantageous paradigm for persistent BMI as it does not require the use of external stimuli; its classes are based on imagined motor activities such as opening and closing a hand or moving feet [14, 15]. With MI, specified motor imagery tasks can result in sensorimotor rhythm fluctuations in the corresponding motor cortex region, which can be measurable with EEG.

Experimental Results and Examples #2

Steady-State Visually Evoked Potentials (SSVEP) Study Overview. A second study was conducted to evaluate a wireless soft bioelectronic system and VR-based SSVEP detection platform. FIGS. 8A, 8B, 8C, 8D, 8E, 8F, 8G each shows aspects of a study to develop virtual reality (VR) implementation for SSVEP training and real-time control using the example EEG brain-machine-interface system in accordance with an illustrative embodiment.

In the study, a platform was configured for split-eye asynchronous stimuli operation and evaluated for information-throughput as a portable brain-computer interface (BCI). The study confirmed, among other things, that a VR interface with 33 stimuli classes can be performed in a real-time, wireless recording of SSVEP for text spelling. The soft wearable platform included a flexible circuit, stretchable interconnectors, and dry needle electrodes; they operated together with a VR headset to provide the fully portable wireless BCI. The study also demonstrated that the skin-conformal electrodes provide biocompatible, consistent skin-electrode contact impedance for a high-quality recording of SSVEP. Compared to the conventional tethered EEG system, the exemplary wireless soft electronic system showed superior performance in the SSVEP recording. The Spatial CNN classification method, integrated with the soft electronics, provided real-time data processing and classification, showing accuracy from 78.93% for 0.8 seconds to 91.73% for 2 seconds with 33 classes from nine human subjects. In addition, the bioelectronic system with only four EEG recording channels demonstrated high ITR performances (243.6±12.5 bit/min) compared to prior works, allowing for a successful demonstration of VR text spelling and navigation in a real-world environment.

The study also showed that excellent signal reproduction with minimal artifacts could be caused by the monolithic and compliant nature of soft circuitries for SSE. In conventional systems with rigid electronics and inflexible wiring, motion can cause stress concentration at the skin-electrode interface. These stresses, when combined with conventional gel-based electrodes, cause significant skin-electrode impedance variations, resulting in motion artifacts. Where dangling wires are involved, the influence of gravity compounds these issues. The studied FMNEs in the SSE application were observed to provide improved SNR by penetrating through the most superficial skin layers composed of dry and dead skin cells. By penetrating these layers and placing the conductive portion of the electrodes well within the dermis, the system could significantly reduce the impedance density while allowing for smaller electrodes than in the conventional setting and improving spatial resolution for MI detection. When compared head-to-head against the gold-standard Ag/AgCl gel electrodes, the FMNE achieved superior SNR.

Methodology. The study used a soft bioelectronic system with multiple components, including a VR headset, dry needle electrodes (e.g., 102), stretchable interconnectors (e.g., 109), and wireless flexible circuits (e.g., 110). The study conducted mechanical reliability of the various components. The study also evaluated the performance of different electrodes for SSVEP stimulus setups.

The training setup involved a subject wearing the VR head-mounted display (HMD) with the straps placed over the electrodes. A subject can wear the soft electronics with dry needle electrodes (hairy site) and wireless circuit (neck), secured by a headband, along with the VR HMD for recording brain signals.

Data were sampled at 500 Hz using a custom-built EEG system for multiple datasets. Once the VR headset was placed on the subject, the application is remotely controlled from a data acquisition Android device. The stimuli were presented simultaneously in a grid to the subject to avoid bias (Xiao et al. 2021). The subject started with their eyes closed for each trial to record alpha rhythms for 8 seconds. At the end of this period, a short beep was sounded, and the subject opened their eyes to look at the stimuli. The subject would shift their eyes to the next stimulus every two seconds, as indicated by a loud click noise. The stimuli temporarily disabled flickering for 0.6 seconds to allow the subject to shift their respective gaze to the next target. The process continues until all the stimuli are viewed, and the subject is prompted to close their eyes for the cycle to restart. For the shorter time frames (<2 sec), only the first 0.8, 1.0, or 1.2 seconds of the stimulus are used to classify the data. Therefore, the number of samples is identical for each time frame and can be calculated as $N=S \times 40$, where S is the number of stimuli. It should be understood that the time periods and numbers of samples described herein are intended only as non-limiting examples and that different time periods can be used in some embodiments.

Figure 8A:
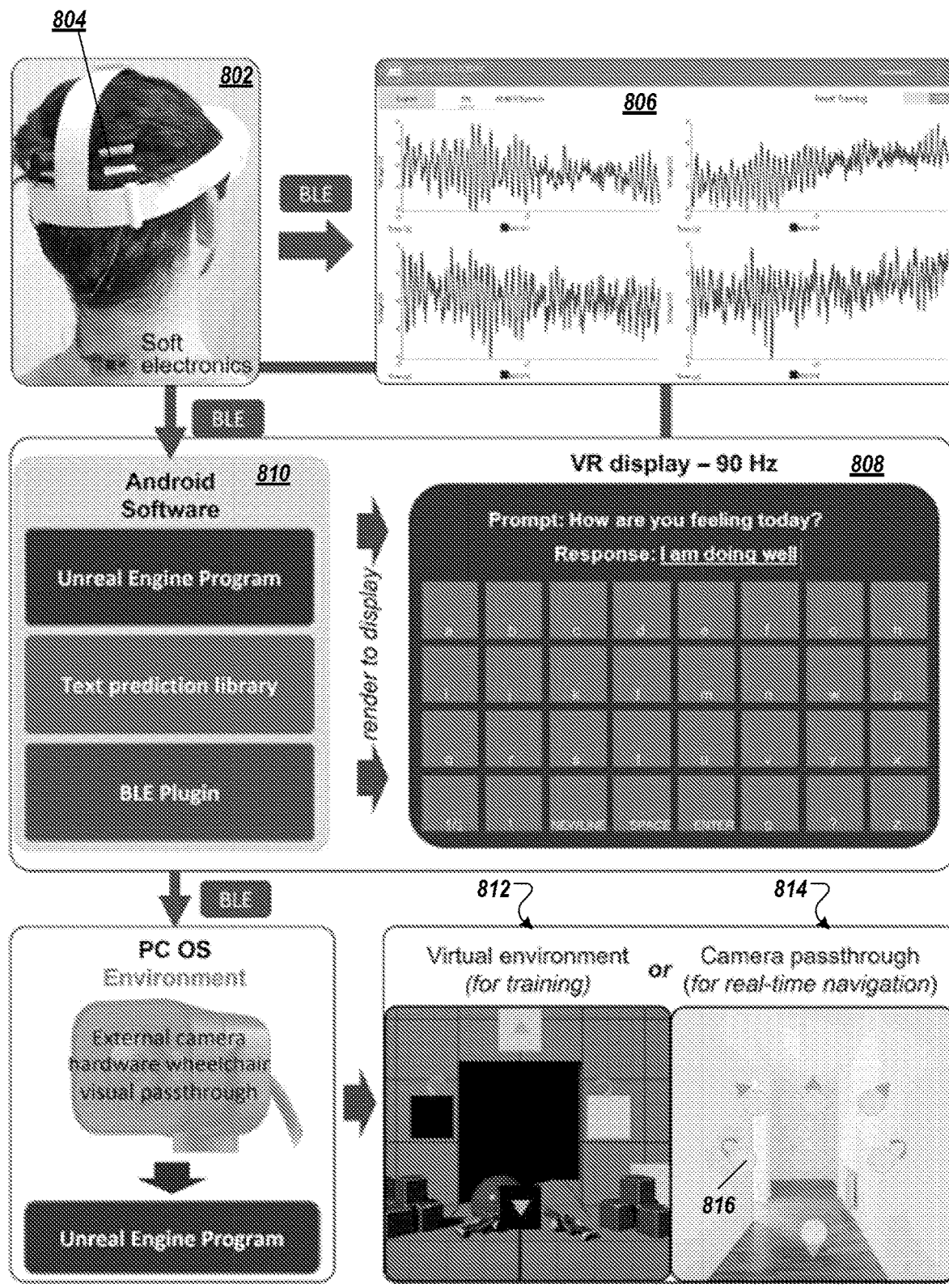
FIGS. 8A, 8B, 8C, 8D, 8E, 8F, 8G each shows aspects of a study to develop virtual reality (VR) implementation for SSVEP training and real-time control using the example EEG brain-machine-interface system in accordance with an illustrative embodiment.

FIG. 8A shows a VR text speller developed and evaluated during the study. Photo 802 shows a subject wearing a virtual-reality head-mounted display (VR HMD) and soft electronics 804 for a BCI demonstration. Plot 806 shows an example measured EEG data from four EEG channels that were transferred via Bluetooth (BLE) communication to a central processor (Android) where the signals are processed and classified in real-time.

Computer rendered output (808) shows the text-speller interface generated in the VR environment by the exemplary system employed in the study. Flow diagram (810) shows the operation flow of the Android software developed for the BCI demonstration that was used to generate the text-speller interface (808). In the system, the Unreal Engine program (further discussed below) was employed to render the text speller software and stimulus overlay to the user. The software included operations for a passthrough camera to allow for the navigation of a real-world environment via an augmented reality viewport using an electric wheelchair. The study implemented the system on two sets of hardware: a VR-HMD viewport (812) and the augmented reality viewport (814). In the augmented reality viewport, the SSVEP commands can be utilized for navigation control (816).

Figure 8B:
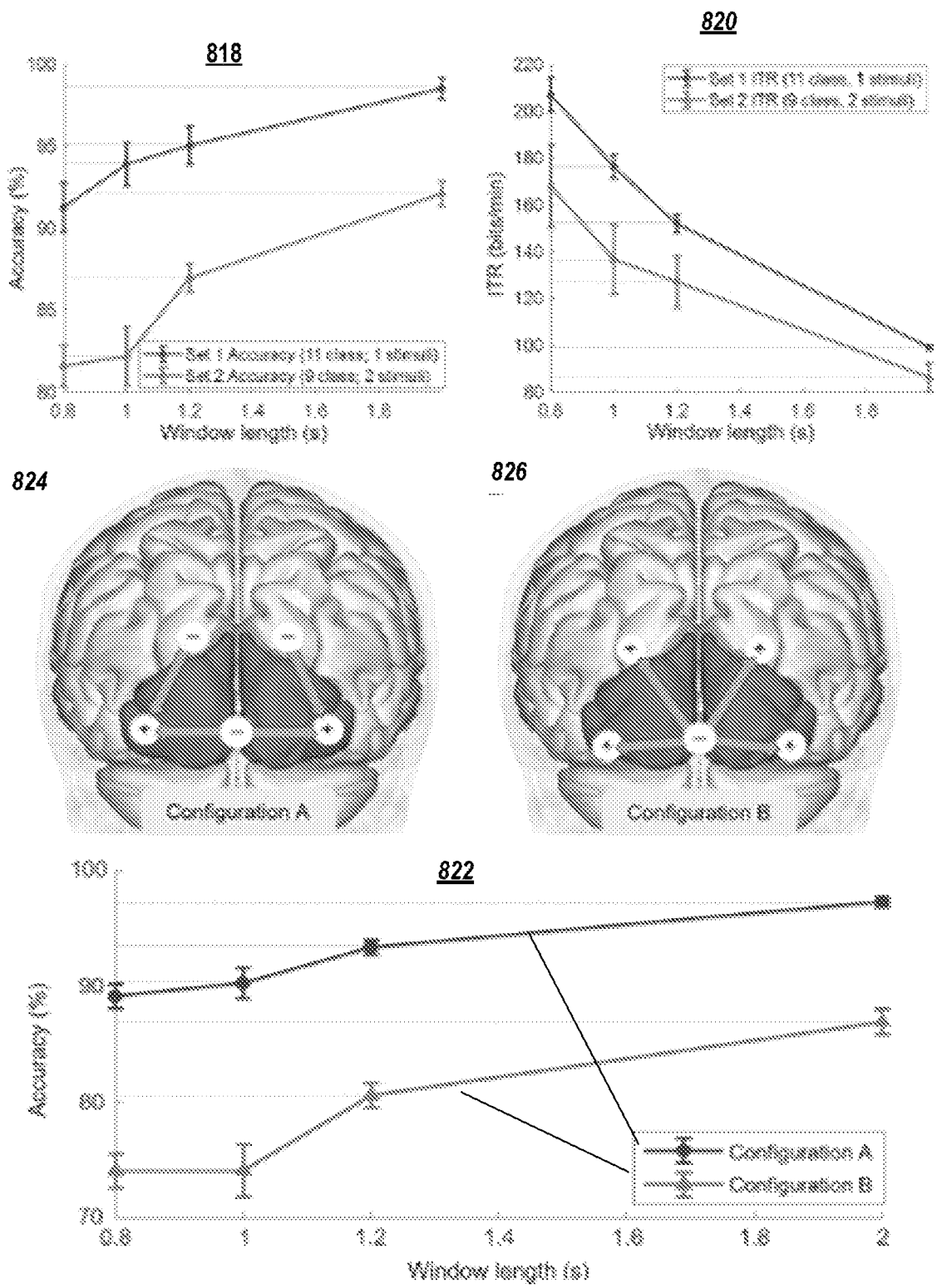

The split-eye asymmetric stimuli (SEAS) platform was generated with a widely used cross-platform software development engine (Unreal Engine 4.26, Epic Games Inc.) targeting VR hardware (Oculus Quest 2, Facebook). Using the "materials" property which can be applied to 2D or 3D objects in the engine, the study created materials that appear differently depending on which size of the VR panel they are being rendered. Materials can be animated using "sprites," which are animated raster graphics, where consecutive frames are arranged in an n×n "sheet." Using the Unreal Engine's built-in texture animation feature, these frames were extracted and rendered. These materials were used to animate most 2D or 3D objects and flat surfaces in the engine environment. The first step was to generate the sheets with the relevant frames based on the frame rate. Here, a program was devised in MATLAB to generate the sinusoidal waveform, convert that waveform into a tile, with the brightness based on the sine wave's amplitude, then arrange those tiles into a 10×10 "sheet" for Unreal Engine's texture rendering system. FIGS. 8F and 8G include the MATLAB code and specific instructions for Unreal Engine to generate the VR interface. In FIG. 8G, an example of a stimulus tile generation is shown with the waveforms and the corresponding tile layout in 10×10 sprites.

The cross-platform software (Unreal Engine, Epic Games) was used to develop an animated texture that appears differently on the left- and right-hand sides of the VR panel. For the first set of tests (referred to as 'Set 1'), ten standard stimuli between 10.0 and 17.2 Hz were generated to determine the separability of SSVEP stimuli. Table 2 shows the left and right eye frequencies and phases.

All stimuli for the VR interface were generated programmatically based on the required frequency and phase offset. The 32 stimuli and their frequencies used in the study are shown and discussed in relation to FIG. 3C. For 16 of the 32 stimuli, two frequencies were used: the first for the left eye and the second for the right.

TABLE 2

| Class # | Left Freq. (Hz) | Left Phase ($\pi$) | Right Freq. (Hz) | Right Phase ($\pi$) |
|---|---|---|---|---|
| 0 | Eyes closed (not SSVEP) | | | |
| 1 | 10.0 | 0.00 | same | same |
| 2 | 10.8 | 1.75 | same | same |
| 3 | 11.6 | 1.50 | same | same |
| 4 | 12.4 | 1.25 | same | same |
| 5 | 13.2 | 1.00 | same | same |
| 6 | 14.0 | 0.75 | same | same |
| 7 | 14.8 | 0.50 | same | same |
| 8 | 15.6 | 0.25 | same | same |
| 9 | 16.4 | 1.85 | same | same |
| 10 | 17.2 | 1.60 | same | same |

Another test set ('Set 2') includes the left eye frequencies range between 10.0 and 17.7 Hz, and the right eye frequencies range between 16.9 and 9.2 Hz, respectively, as shown in Table 3.

TABLE 3

| Class # | Left Freq. (Hz) | Left Phase ($\pi$) | Right Freq. (Hz) | Right Phase ($\pi$) |
|---|---|---|---|---|
| 0 | Eyes closed (not SSVEP) | | | |
| 1 | 10.0 | 0.00 | same | same |
| 2 | 10.8 | 1.75 | same | same |
| 3 | 11.6 | 1.50 | same | same |
| 4 | 12.4 | 1.25 | same | same |
| 5 | 13.2 | 1.00 | same | same |
| 6 | 14.0 | 0.75 | same | same |
| 7 | 14.8 | 0.50 | same | same |
| 8 | 15.6 | 0.25 | same | same |
| 9 | 16.4 | 1.85 | same | same |
| 10 | 17.2 | 1.60 | same | same |

Due to the complexity of the stimuli under study and to maintain a high level of classification performance, machine learning in the study was performed on a per-session basis. Example descriptions are provided in relation to FIG. 4B. During the training, in the range of 0.8-2 s, the data was bidirectionally filtered using a 3rd order high-pass Butterworth filter with a corner frequency of 2.0 Hz. The data were linearly rescaled to the range of [−0.5, 0.5] across the training dataset, so the resulting values are in the range of [0, 1]. This type of preprocessing could cause issues for the conventional Ag/AgCl electrodes as the signal amplitudes change over time, diminishing electrode performance. However, the exemplary dry needle electrodes in soft electronics can achieve consistent performance with enhanced skin contact. This simplified preprocessing while improving classification performance.

In the study using conventional Ag/AgCl electrodes, each subjects' skin was cleaned by gently rubbing with an alcohol wipe, and dead skin cells were removed using an abrasive gel (NuPrep, Weaver, and Co.) in order to maintain a contact impedance below 10 k$\Omega$ on all electrodes. The abrasive gel was removed using an alcohol wipe and the surface dried using a clean paper towel. For the FMNEs, the only skin preparation conducted was a gentle rub of the electrode location with an alcohol wipe. The EEG data were recorded using a custom application running on an Android Tablet (Samsung Galaxy Tab S4), using Bluetooth Low Energy wireless communication.

Preliminary SSVEP Performance. FIG. 8B shows the results of a preliminary performance evaluation for different electrode positions. Preliminary SSVEP and SEAS tests were performed in order to test the feasibility of using stimuli in the VR environment before running a text speller setup with 32 stimuli. Plot 818 shows the average classification accuracies for two SSVEP stimulation sets across multiple time windows (0.8-2 seconds). Plot 820 shows the average information transfer rate (ITR) for the two SSVEP stimulation sets from eight subjects (N=440 for Set 1 and N=360 for Set 2). For the first set of tests (labeled as 'Set 1', per Table 2), ten standard stimuli between 10.0 and 17.2 Hz were generated to determine the separability of SSVEP stimuli (details in Table S1). Another test set ('Set 2', per Table 3) includes the left eye frequencies range between 10.0 and 17.7 Hz, and the right eye frequencies range between 16.9 and 9.2 Hz, respectively.

Results from Set "1" show high accuracies with short-time samples. For example, in a basic cue-guided task, eight subjects in Set 1 demonstrate 91.25±1.40% accuracy at a window length of only 0.8 seconds. This result shows a high-throughput ITR, 206.7±7.3 bits/min. With an increased window length, the overall accuracy increases significantly 93.88±1.11% at 1.0 sec, 95.03±0.97% at 1.2 sec, and 98.50±0.34% at 2.0 sec.

FIG. 8B also show the results of the evaluation of two configurations (configuration "A" 824, configuration "B" 826) of the electrode positions. Plot 822 shows the results comparing the classification accuracy between the two electrode arrangements. From the plot (822), it can be observed that configuration "A" demonstrated stronger performance than configuration "B" for the subjects that were evaluated. Error bars in graphs represent the standard error of the mean. In configuration "A" 824, two channels are biased to each one respective hemisphere. In configuration "B" 826, all channels share a central reference.

Based on the study, a new stimulation setup was developed, 'Set 3', using 32-unique frequency combinations to minimize conflict and prevent inaccuracies as studied from the setup, 'Set 2'. The details of this stimulus setup are discussed in relation to FIG. 3C.

Information transfer rate (ITR), measured in bits per minute, can be used to assess BCI performance. ITR is calculated based on the number of targets, the average time required to relay command, and the classification accuracy per Equation 1.

$$ITR = \left(\log_2 N + A\log_2 A + (1-A)\log_2\left(\frac{1-A}{N-1}\right)\right) \times \left(\frac{60}{w}\right) \frac{\text{bits}}{\min} \quad \text{(Eq. 1)}$$

where N is the number of targets, A is the accuracy, and w is the total time required to execute a command, including data acquisition time plus processing, classification, and execution latencies.

CNN Classification Performance. To train the CNN, testing data were segmented on the initial time the stimulus was presented. For each time frame (0.8-1.2 s), only the first period was used, and the rest was discarded. After segmenting, the data was preprocessed using a 3rd-order Butterworth high-pass filter with a corner frequency of 2.0 Hz. The data was not preprocessed before being used in training and classification. For Sets "1"-"2", the samples, N, were subdivided into groups of 10 for cross-fold validation. For Set "3", the samples N were subdivided into groups of 4 for 4-fold cross-validation for faster setup times. The classification was performed using a convolutional neural network (CNN) with spatial convolutions (Bevilacqua et al. 2014; Mahmood et al. 2021; Ravi et al. 2020; Waytowich et al. 2018). For the CNN, a batch size of 128 samples was used, and the training was run for 100 epochs or aborted early if the classification of the validation data did not improve for 10 epochs. The trained network with the highest performing classification accuracy was saved for use in real-time classification.

Figure 8C:
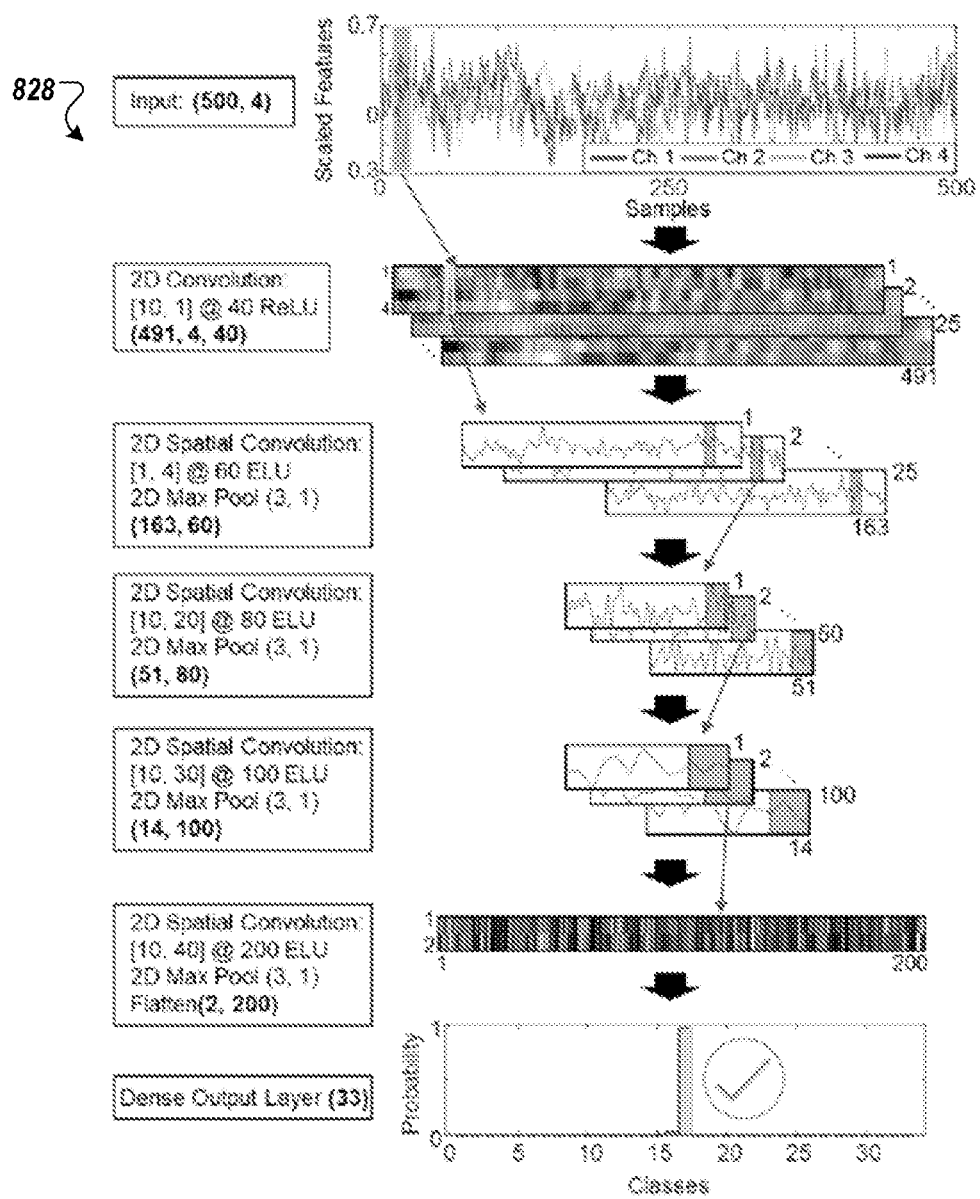
Figure 8C:
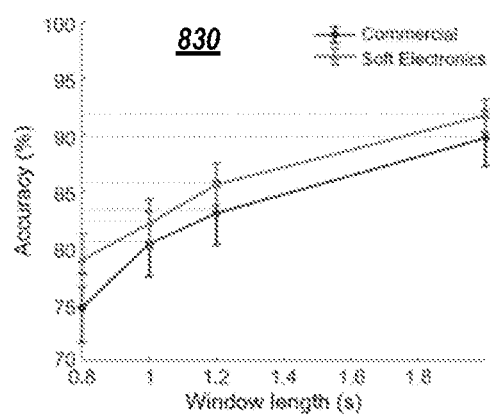
Figure 8C:
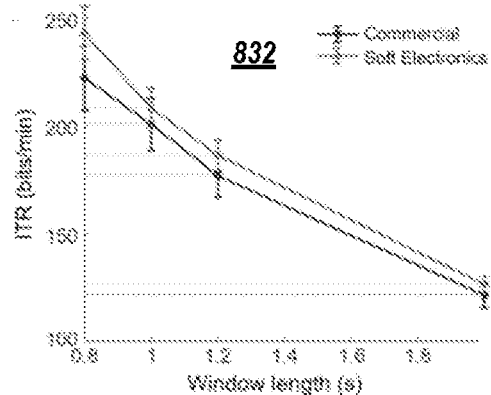

FIG. 8C shows the results of the classification performance for the CNN classifier used in the study. The CNN classifier employed a spatial-CNN classification. In FIG. 8C, an overview 828 of the spatial CNN model is shown, which includes its various hidden layers and their extracted features from a 1-sec segment of 4-channel EEG signals. The study used a stimulus setup having a left stimulation frequency of 8.2 Hz and a right stimulation frequency of 13.2 Hz.

The study conducted two sets of experiments using a commercial setup with wired Ag/AgCl electrodes (Norton et al. 2015) and exemplary wireless soft electronics. Both setups used 4 EEG channels and 33 classes. The conventional setup used wired standard electrode leads and Ag/AgCl electrodes interfaced with conductive paste to record EEG signals on the scalp. The exemplary soft electronic system used the dry needle electrodes with a headband without conductive gels, e.g., as described in relation to FIG. 2.

Plots 830 and 832 each shows the performance results for the two set of experiments. Plot 830 shows the classification accuracy, and plot 832 shows the average ITR for each of the two sets of experiments. Using 4-fold cross-validation, the commercial setup showed (via plots 830 and 832, respectively) 74.72±3.03% accuracy from 0.8 sec of data (ITR: 222.4±15.0 bits/min). Longer time lengths were observed to offer slightly higher accuracy expected. In contrast, the exemplary soft electronic system showed (via plots 830 and 832, respectively) a substantial increase in the classification accuracy and ITR with 78.93±2.36% and 243.6±12.5 bits/min, respectively. Overall, this study demonstrates the unique advantage of using the wireless soft platform with dry electrodes over the conventional tethered system with required skin preparation and wired electrodes.

Figures 8D, 8E:
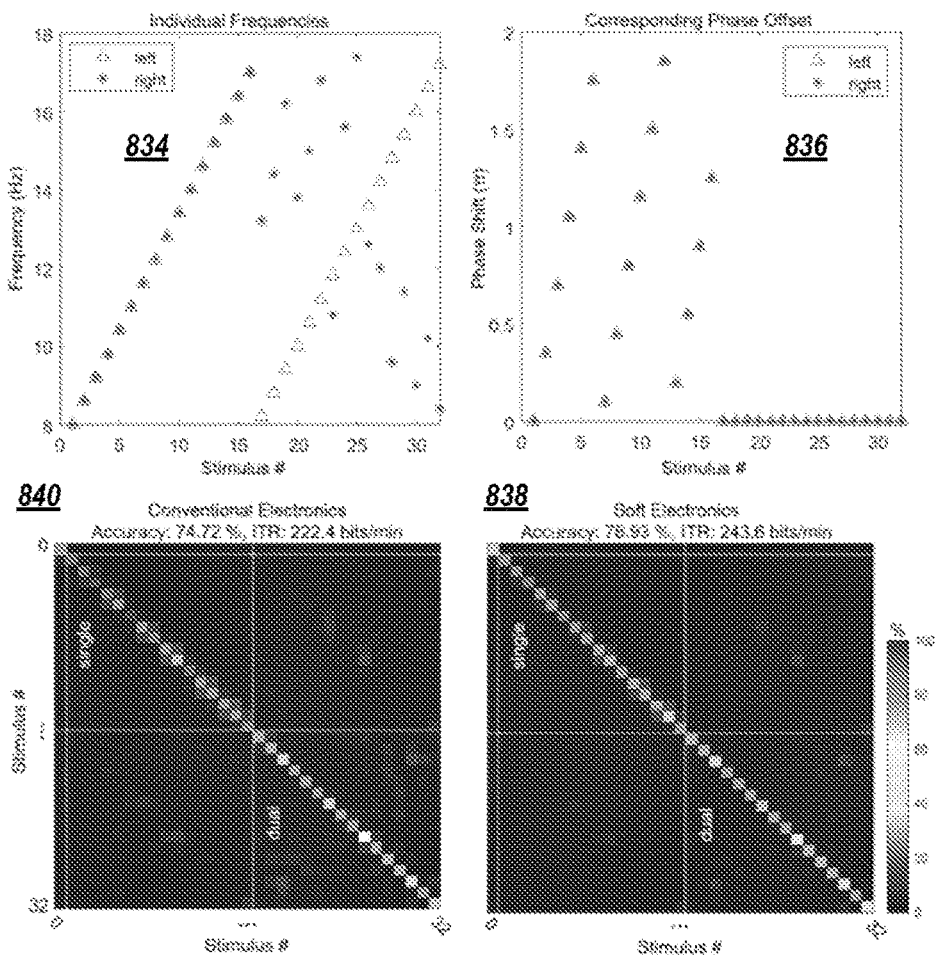
Figure 8F:
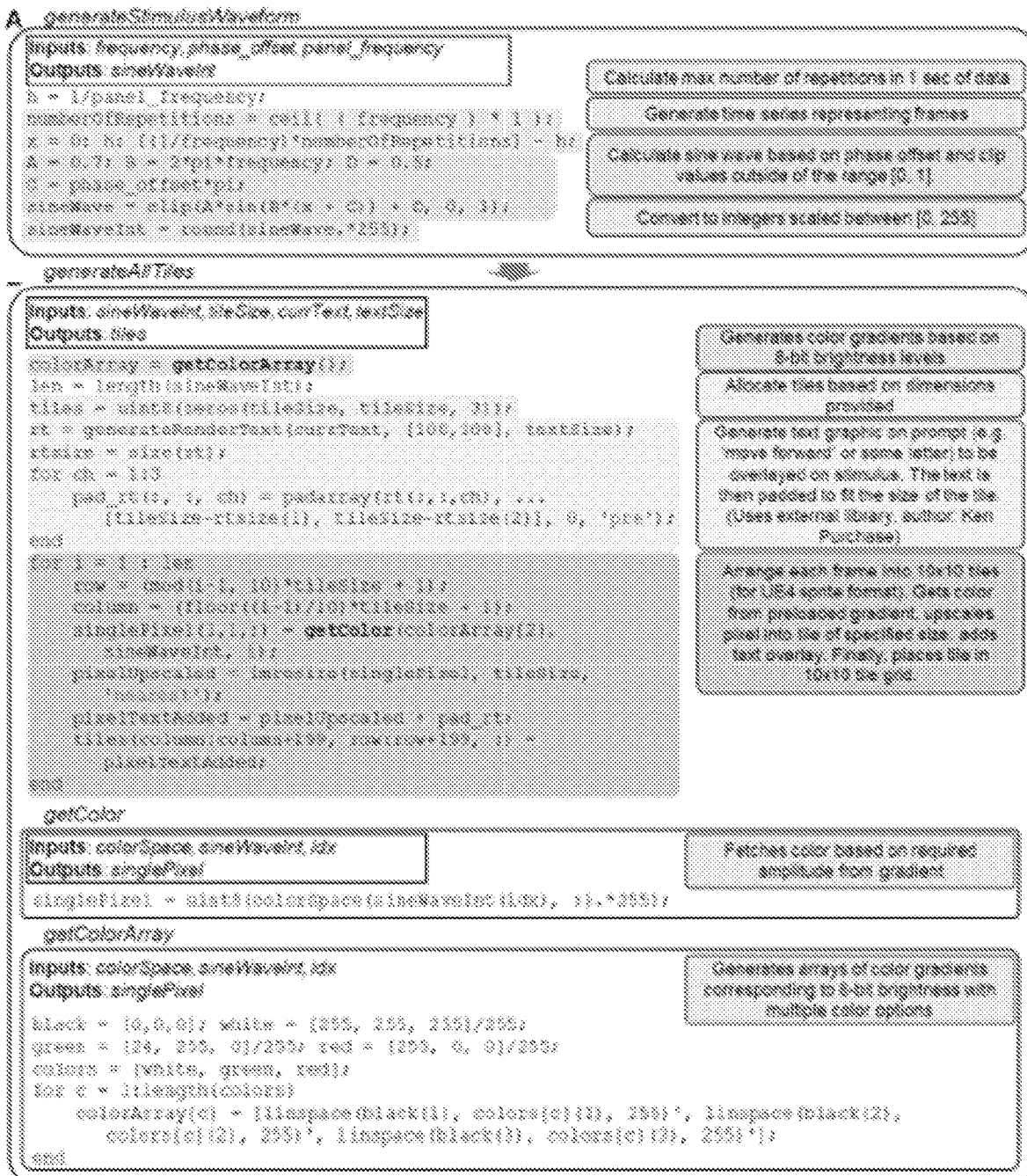
Figure 8G:
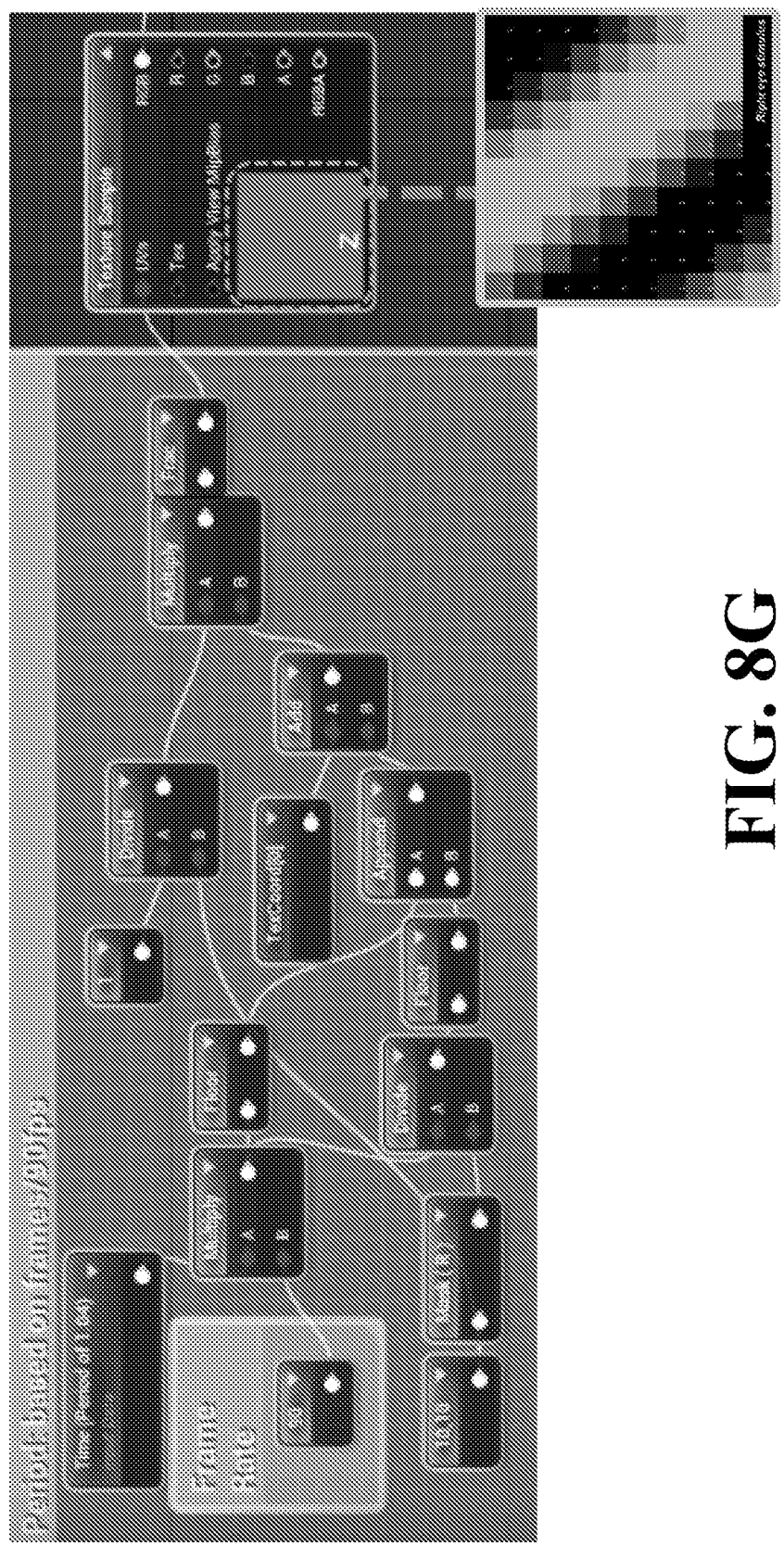

Stimuli Frequency and Phase Shift Characterization. FIG. 8D shows the results of an evaluation of the effects of stimuli frequency and phase shift. The study was performed using the conventional and exemplary soft electronics setups. Plot 834 shows the left- and right-eye frequency response corresponding to consecutive stimuli visualized, and plot 836 shows the corresponding left- and right-eye phase offsets.

Plot 838 shows a confusion matrix generated from the results of the soft electronics for a 33-class SEAS stimuli (for nine subjects). Plot 840 shows the same results under the same experimental conditions for the conventional setup. It can be observed that for the single-frequency stimuli, most of the confusion is from neighboring frequencies. In contrast, dual-frequency stimuli have various mixing with both single and other dual-frequency stimuli. This result showed that stimuli from one eye or the other are processed in both hemispheres of the visual cortex. In addition, the study also demonstrated that there are significant hemisphere-related asynchronies and mixing to which classification can be performed. The result shows, at a high level, one of the highest ITRs with as few as 4 EEG channels, compared to prior work.

FIG. 8E shows a table of comparative performance between the exemplary soft electronics and prior works. As shown in the table, the exemplary soft electronics can achieve a ITR of 243.5 bits/minute for 33 classifications using 4 electrode channels with an accuracy near 80%.

SSVEP Discussion. Locked-in syndrome (LIS) describes a state of complete paralysis apart from blinking and eye movement (Padfield et al. 2019). Here, brain activity and cognitive function are usually unaffected, resulting in a state of pseudo-coma where a subject can neither move nor communicate but are aware of their consciousness and environment. Despite normal cortical brain activity, subjects cannot control motor function, typically due to injury to the lower brain and brainstem. There are several causes of LIS in humans, including but not limited to: stroke of the brainstem, traumatic brain injury or hemorrhage, poisoning, or drug overdose. Brain activity analysis is typically used to diagnose LIS with instruments such as electroencephalography (EEG) to observe the sleep-wake patterns of the affected individuals. The emergence of BCI allows subjects to bypass the requirement for motor function, controlling machines such as computers or prosthetic devices by monitoring brain activity. BCIs offer a potential solution to subjects with a severe physical disability such as LIS or quadriplegia, restoring some movement and communication to these individuals and improving quality of life. EEG design for BCI has trended towards wearables with wireless functionality since the standardization of common wireless protocols such as Bluetooth (Lin et al. 2010). Dry electrodes offer excellent, consistent long-term performance compared with gel-based electrodes (Norton et al. 2015; Salvo et al. 2012; Stauffer et al. 2018); provided the skin preparation, and amplifier, shielding, and electrode configurations are adequate (Li et al. 2017; Salvo et al. 2012). Lightweight sensors with minimal cabling also greatly reduce dragging or movement artifacts with poorly configured conventional EEG (Tallgren et al. 2005).

With SSVEP, up to 40 unique stimuli with varying frequencies and phase offsets can be distinguished with reasonable accuracy (Nakanishi et al. 2017). Empirical evidence suggests significant hemispheric asymmetries in SSVEP signals (Martens and Hübner 2013; Wu 2016). Recent work demonstrated asymmetric high-frequency dual-stimuli SSVEP, where two stimuli are used flickering at alternative phases, demonstrating more efficient SSVEP encoding (Yue et al. 2020). Due to the asymmetric nature of the connection between the eyes' sensory receptors and visual cortex, it may be inferred that different stimuli simultaneously viewed by each eye confer measurably different brain activity in either hemisphere (Richard et al. 2018).

Embodiments of the present disclosure include portable VR-enabled BCIs using a soft bioelectronic system and the SEAS platform to use SSVEP. VR can be used to simultaneously present asynchronous SSVEP stimuli-different frequencies to each eye. Overall, the use of novel stimuli with VR along with the soft, wearable wireless device enables a 33-class high-throughput SSVEP BCI with high accuracy and low control latency. Using only four channels, an accuracy of 78.93±1.05% for 0.8 seconds of data for a peak information transfer rate of 243.6±12.5 bits/min was observed to be achieved. In the high-accuracy mode, the device achieves 91.73±0.68% for two seconds of data at a throughput of 126.6±3.7 bits/min. This performance is demonstrated using a real-time text speller interface using a full keyboard-type setup.

Although example embodiments of the present disclosure are explained in some instances in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an," and "the" include plural referents unless the context clearly dictates otherwise. Ranges may be expressed herein as from "about" or "5 approximately" one particular value and/or to "about" or "approximately" another particular value. When such a range is expressed, other exemplary embodiments include from the one particular value and/or to the other particular value.

By "comprising" or "containing" or "including" is meant that at least the name compound, element, particle, or method step is present in the composition or article or method but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

As discussed herein, a "subject" may be any applicable human, animal, or other organism, living or dead, or other biological or molecular structure or chemical environment, and may relate to particular components of the subject, for instance, specific tissues or fluids of a subject (e.g., human tissue in a particular area of the body of a living subject), which may be in a particular location of the subject, referred to herein as an "area of interest" or a "region of interest."

It should be appreciated that, as discussed herein, a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to humans (e.g., rat, dog, pig, monkey), etc. It should be appreciated that the subject may be any applicable human patient, for example.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 10% of the numerical value of the number with which it is being used. Therefore, about 50% means in the range of 45%-55%. Numerical ranges recited herein by endpoints include all numbers and fractions subsumed within that range (e.g., 1 to 5 includes 1, 1.5, 2, 2.75, 3, 3.90, 4, 4.24, and 5).

Similarly, numerical ranges recited herein by endpoints include subranges subsumed within that range (e.g., 1 to 5 includes 1-1.5, 1.5-2, 2-2.75, 2.75-3, 3-3.90, 3.90-4, 4-4.24, 4.24-5, 2-5, 3-5, 1-4, and 2-4). It is also to be understood that all numbers and fractions thereof are presumed to be modified by the term "about."

The following patents, applications, and publications, as listed below and throughout this document, are hereby incorporated by reference in their entirety herein.

[1] N. Padfield, J. Zabalza, H. Zhao, V. Masero, J. Ren, Sensors 2019, 19, 1423.

[2] A. Venkatakrishnan, G. E. Francisco, J. L. Contreras-Vidal, Current physical medicine and rehabilitation reports 2014, 2, 93.

[3] M. Mahmood, D. Mzurikwao, Y.-S. Kim, Y. Lee, S. Mishra, R. Herbert, A. Duarte, C. S. Ang, W.-H. Yeo, Nature Machine Intelligence 2019, 1, 412.

[4] Norton et al, "Soft, curved electrode systems capable of integration on the auricle as a persistent brain-computer interface," Proceedings of the National Academy of Sciences 2015, 112, 3920.

[5] Herbert et al, "Soft Material-Enabled, Flexible Hybrid Electronics for Medicine, Healthcare, and Human-Machine Interfaces," Advanced Materials 2020, 32, 1901924; W.-H. Yeo, Y. Lee, Journal of Nature and Science 2015, 1, e132.

[6] Lin et al, "Review of Wireless and Wearable Electroencephalogram Systems and Brain-Computer Interfaces—A Mini-Review," Gerontology 2010, 56, 112. [6'] Tian et al, "Large-area MRI-compatible epidermal electronic interfaces for prosthetic control and cognitive monitoring," Nature Biomedical Engineering 2019, 3, 194 [6"] Li et al, "Recent Developments on Graphene-Based Electrochemical Sensors toward Nitrite," J. Wu, Y. Xia, Y. Wu, Y. Tian, J. Liu, D. Chen, Q. He, Journal of neural engineering 2020, 17, 026001.

[7] P. Salvo, R. Raedt, E. Carrette, D. Schaubroeck, J. Vanfleteren, L. Cardon, Sensors and Actuators A: Physical 2012, 174, 96.

[8] G. Li, S. Wang, Y. Y. Duan, Sensors and Actuators B: Chemical 2017, 241, 1244.

[9] F. Stauffer, M. Thielen, C. Sauter, S. Chardonnens, S. Bachmann, K. Tybrandt, C. Peters, C. Hierold, J. Voros, Adv Healthc Mater 2018, 7, e1700994; M. A. Lopez-Gordo, D. Sanchez-Morillo, F. P. Valle, Sensors 2014, 14, 12847.

[10] D. Gao, K. Parida, P. S. Lee, Advanced Functional Materials 2020, 30, 1907184; H. Wu, G. Yang, K. Zhu, S. Liu, W. Guo, Z. Jiang, Z. Li, Advanced Science 2021, 8, 2001938.

[11] W. Guo, P. Zheng, X. Huang, H. Zhuo, Y. Wu, Z. Yin, Z. Li, H. Wu, ACS applied materials & interfaces 2019, 11, 8567.

[12] Z. Jiang, M. O. G. Nayeem, K. Fukuda, S. Ding, H. Jin, T. Yokota, D. Inoue, D. Hashizume, T. Someya, Advanced Materials 2019, 31, 1903446.

[13] R. Abiri, S. Borhani, E. W. Sellers, Y. Jiang, X. Zhao, Journal of neural engineering 2019, 16, 011001.

[14] G. Pfurtscheller, C. Neuper, D. Flotzinger, M. Pregenzer, Electroencephalography and clinical Neurophysiology 1997, 103, 642

[14'] X. Tang, W. Li, X. Li, W. Ma, X. Dang, Expert Systems with Applications 2020, 149, 113285.

[15] R. Zhang, Q. Zong, L. Dou, X. Zhao, Journal of neural engineering 2019, 16, 066004.

[16] V. Jurcak, D. Tsuzuki, I. Dan, Neuroimage 2007, 34, 1600.

[17] O. Olatunji, A. Denloye, Journal of Polymers and the Environment 2019, 27, 1252; A. Römgens, D. Bader, J. Bouwstra, F. Baaijens, C. Oomens, journal of the mechanical behavior of biomedical materials 2014, 40, 397.

[18] S. Russo, T. Ranzani, H. Liu, S. Nefti-Meziani, K. Althoefer, A. Menciassi, Soft robotics 2015, 2, 146

[18'] W. H. Yeo, Y. S. Kim, J. Lee, A. Ameen, L. Shi, M. Li, S. Wang, R. Ma, S. H. Jin, Z. Kang, Advanced materials 2013, 25, 2773.

[19] H. Yang, S. Sakhavi, K. K. Ang, C. Guan, "On the use of convolutional neural networks and augmented CSP features for multi-class motor imagery of EEG signals classification", presented at 2015 37th Annual International Conference of the IEEE Engineering in Medicine and Biology Society (EMBC), 2015; S. Chaudhary, S. Taran, V. Bajaj, A. Sengur, IEEE Sensors Journal 2019, 19, 4494.

[20] Z. Tang, C. Li, S. Sun, Optik 2017, 130, 11.

[21] R. T. Schirrmeister, J. T. Springenberg, L. D. J. Fiederer, M. Glasstetter, K. Eggensperger, M. Tangermann, F. Hutter, W. Burgard, T. Ball, Human brain mapping 2017, 38, 5391.

[22] P. Welch, IEEE Transactions on audio and electroacoustics 1967, 15, 70.

[23] Y.-T. Kwon, H. Kim, M. Mahmood, Y.-S. Kim, C. Demolder, W.-H. Yeo, ACS Appl. Mater. Interfaces 2020, 12, 49398; Y.-T. Kwon, J. J. Norton, A. Cutrone, H.-R. Lim, S. Kwon, J. J. Choi, H. S. Kim, Y. C. Jang, J. R. Wolpaw, W.-H. Yeo, Biosens. Bioelectron. 2020, 165, 112404.

[24] M. Abadi, P. Barham, J. Chen, Z. Chen, A. Davis, J. Dean, M. Devin, S. Ghemawat, G. Irving, M. Isard, "Tensorflow: A system for large-scale machine learning", presented at 12th {USENIX} symposium on operating systems design and implementation ({OSDI} 16), 2016.

[25] Y. R. Tabar, U. Halici, Journal of neural engineering 2016, 14, 016003.

[26] N. Lu, T. Li, X. Ren, H. Miao, IEEE transactions on neural systems and rehabilitation engineering 2016, 25, 566.

[27] Z. Shi, F. Zheng, Z. Zhou, M. Li, Z. Fan, H. Ye, S. Zhang, T. Xiao, L. Chen, T. H. Tao, Y.-L. Sun, Y. Mao, Advanced Science 2019, 6, 1801617.

[28] Bevilacqua, V., Tattoli, G., Buongiorno, D., Loconsole, C., Leonardis, D., Barsotti, M., Frisoli, A., Bergamasco, M., 2014. A novel BCI-SSVEP based approach for control of walking in virtual environment using a convolutional neural network. 2014 International Joint Conference on Neural Networks (IJCNN), pp. 4121-4128. IEEE.

[29] Chen, X., Wang, Y., Nakanishi, M., Gao, X., Jung, T. P., Gao, S., 2015. High-speed spelling with a noninvasive brain-computer interface. Proc Natl Acad Sci USA 112 (44), E6058-6067.

[30] Kwak, N. S., Muller, K. R., Lee, S. W., 2017. A convolutional neural network for steady state visual evoked potential classification under ambulatory environment. PLOS One 12 (2), e0172578.

[31] Li, G., Wang, S., Duan, Y. Y., 2017. Towards gel-free electrodes: A systematic study of electrode-skin impedance. Sensors and Actuators B: Chemical 241, 1244-1255.

[32] Lin, C. T., Ko, L. W., Chang, M. H., Duann, J. R., Chen, J. Y., Su, T. P., Jung, T. P., 2010. Review of wireless and wearable electroencephalogram systems and brain-computer interfaces—a mini-review. Gerontology 56 (1), 112-119.

[33] Mahmood, M., Kwon, S., Kim, Y.-S., Siriaraya, P., Choi, J., Boris, O., Kang, K., Jun Yu, K., Jang, Y. C., Ang, C. S., 2021. Wireless Soft Scalp Electronics and Virtual Reality System for Motor Imagery-based Brain-Machine Interfaces. Advanced Science.

[34] Mahmood, M., Mzurikwao, D., Kim, Y.-S., Lee, Y., Mishra, S., Herbert, R., Duarte, A., Ang, C. S., Yeo, W.-H., 2019. Fully portable and wireless universal brain-machine interfaces enabled by flexible scalp electronics and deep learning algorithm. Nature Machine Intelligence 1 (9), 412-422.

[35] Martens, U., Hübner, R., 2013. Functional hemispheric asymmetries of global/local processing mirrored by the steady-state visual evoked potential. Brain and cognition 81 (2), 161-166.

[36] Nakanishi, M., Wang, Y., Chen, X., Wang, Y.-T., Gao, X., Jung, T.-P., 2017. Enhancing detection of SSVEPs for a high-speed brain speller using task-related component analysis. IEEE Transactions on Biomedical Engineering 65 (1), 104-112.

[37] Norton, J. J. S., Lee, D. S., Lee, J. W., Lee, W., Kwon, O., Won, P., Jung, S.-Y., Cheng, H., Jeong, J.-W., Akce, A., Umunna, S., Na, I., Kwon, Y. H., Wang, X.-Q., Liu, Z., Paik, U., Huang, Y., Bretl, T., Yeo, W.-H., Rogers, J. A., 2015. Soft, curved electrode systems capable of integration on the auricle as a persistent brain-computer interface. Proceedings of the National Academy of Sciences 112 (13), 3920-3925.

[38] Padfield, N., Zabalza, J., Zhao, H., Masero, V., Ren, J., 2019. EEG-based brain-computer interfaces using motor-imagery: Techniques and challenges. Sensors 19 (6), 1423.

[39] Ravi, A., Beni, N. H., Manuel, J., Jiang, N., 2020. Comparing user-dependent and user-independent training of CNN for SSVEP BCI. Journal of neural engineering 17 (2), 026028.

[40] Richard, B., Chadnova, E., Baker, D. H., 2018. Binocular vision adaptively suppresses delayed monocular signals. NeuroImage 172, 753-765.

[41] Rodeheaver, N., Herbert, R., Kim, Y. S., Mahmood, M., Kim, H., Jeong, J. W., Yeo, W. H., 2021. Strain-Isolating Materials and Interfacial Physics for Soft Wearable Bioelectronics and Wireless, Motion Artifact-Controlled Health Monitoring. Advanced Functional Materials 31 (36), 2104070.

[42] Rodeheaver, N., Kim, H., Herbert, R., Seo, H., Yeo, W.-H., 2022. Breathable, Wireless, Thin-Film Wearable Biopatch Using Noise-Reduction Mechanisms. ACS Applied Electronic Materials.

[43] Salvo, P., Raedt, R., Carrette, E., Schaubroeck, D., Vanfleteren, J., Cardon, L., 2012. A 3D printed dry electrode for ECG/EEG recording. Sensors and Actuators A: Physical 174, 96-102.

[44] Stauffer, F., Thielen, M., Sauter, C., Chardonnens, S., Bachmann, S., Tybrandt, K., Peters, C., Hierold, C., Voros, J., 2018. Skin Conformal Polymer Electrodes for Clinical ECG and EEG Recordings. Adv Healthc Mater 7 (7), e1700994.

[45] Tallgren, P., Vanhatalo, S., Kaila, K., Voipio, J., 2005. Evaluation of commercially available electrodes and gels for recording of slow EEG potentials. Clin Neurophysiol 116 (4), 799-806.

[46] Volosyak, I., 2011. SSVEP-based Bremen-BCI interface—boosting information transfer rates. J Neural Eng 8 (3), 036020.

[47] Wang, Y., Wang, Y. T., Jung, T. P., 2010. Visual stimulus design for high-rate SSVEP BCI. Electronics Letters 46 (15).

[48] Waytowich, N., Lawhern, V. J., Garcia, J. O., Cummings, J., Faller, J., Sajda, P., Vettel, J. M., 2018. Compact convolutional neural networks for classification of asynchronous steady-state visual evoked potentials. Journal of neural engineering 15 (6), 066031.

[49] Wu, Z., 2016. Physical connections between different SSVEP neural networks. Scientific reports 6 (1), 1-9.

[50] Xiao, C., Chiang, K.-J., Nakanishi, M., Jung, T.-P., 2021. A Comparison Study of Single- and Multiple-Target Stimulation Methods for Eliciting Steady-State Visual Evoked Potentials. 2021 10th International IEEE/EMBS Conference on Neural Engineering (NER), pp. 698-701. IEEE.

[51] Xing, X., Wang, Y., Pei, W., Guo, X., Liu, Z., Wang, F., Ming, G., Zhao, H., Gui, Q., Chen, H., 2018. A high-speed SSVEP-based BCI using dry EEG electrodes. Scientific reports 8 (1), 1-10.

[52] Yue, L., Xiao, X., Xu, M., Chen, L., Wang, Y., Jung, T.-P., Ming, D., 2020. A brain-computer interface based on high-frequency steady-state asymmetric visual evoked potentials. 2020 42nd Annual International Conference of the IEEE Engineering in Medicine & Biology Society (EMBC), pp. 3090-3093. IEEE.

[53] Zavanelli, N., Kim, H., Kim, J., Herbert, R., Mahmood, M., Kim, Y.-S., Kwon, S., Bolus, N. B., Torstrick, F. B., Lee, C. S., 2021. At-home wireless monitoring of acute hemodynamic disturbances to detect sleep apnea and sleep stages via a soft sternal patch. Science advances 7 (52), eabl4146.

What is claimed:

1. A system comprising:
a set of low-profile EEG sensors, each comprising an array of flexible epidermis-penetrating microneedle electrodes fabricated on a flexible-circuit substrate, the flexible-circuit substrate operatively connected to an analog-to-digital converter circuitry operatively connected to a wireless interface circuitry; and
a brain-machine interface operatively connected to the set of low-profile EEG sensors, the brain-machine interface comprising:
a processor; and
a memory operatively connected to the processor, the memory having instructions stored thereon, wherein execution of the instructions by the processor causes the processor to:
receive EEG signals acquired from the low-profile EEG sensor;
continuously classify brain signals as control signals via a trained neural network from the acquired EEG signals; and
output the control signals to a virtual reality environment controller to actuate a command in a VR scene generated by the virtual reality environment controller to be viewed by a subject.

2. The system of claim 1, wherein the command causes a set of movements of an extremity in the VR scene, and wherein the trained neural network is configured to classify the brain signals for the set of movements.

3. The system of claim 1, wherein the set of low-profile EEG sensors are connected to the brain-machine interface over a set of stretchable flexible connectors.

4. The system of claim 1, wherein the microneedle electrodes have expanded contact surface area and reduced electrode impedance density.

5. The system of claim 1, further comprising:
a wearable soft headset comprising a low-modulus elastomeric band.

6. The system of claim 1, wherein the trained neural network comprises a spatial convolutional neural network.

7. The system of claim 1, wherein the set of low-profile EEG sensors is placed along a scalp of the subject for motor imagery.

8. The system of claim 1, wherein the set of low-profile EEG sensors is placed along a scalp of the subject for steady-state visually evoked potentials (SSVEP) measurements.

9. The system of claim 8, wherein the virtual reality environment controller to configured to generate split-eye asynchronous stimulus (SEAS) in the virtual scene for a real-time text speller interface.

10. The system of claim 1, wherein the execution of the instructions by the processor further causes the processor to:
transmit the acquired EEG signals to a remote or cloud computing device executing a retraining operation of the trained neural network; and
receive during run-time operation of the virtual reality environment controller an updated trained neural network from the remote or cloud computing device.

11. The system of claim 1, wherein a plurality of the flexible epidermis-penetrating microneedle electrodes of the array each is at least 500 μm in height (e.g., 800 μm) to mount on a hairy scalp with a base width of about 350 μm and has an area of about 36 mm$^2$.

12. A method comprising:
providing a set of low-profile EEG sensors placed at a scalp of a user, wherein the set of low-profile EEG sensors each comprises an array of flexible epidermis-penetrating microneedle electrodes fabricated on a flexible-circuit substrate, the flexible-circuit substrate operatively connected to an analog-to-digital converter circuitry operatively connected to a wireless interface circuitry;
receiving, by a processor or a brain-machine interface operatively connected to the set of low-profile EEG sensors, EEG signals acquired from the low-profile EEG sensor;
continuously classifying, by the processor, brain signals as control signals via a trained neural network from the acquired EEG signals; and
outputting, by the processor, the control signals to a virtual reality environment controller to actuate a command in a VR scene generated by the virtual reality environment controller to be viewed by a subject.

13. The method of claim 12, wherein the set of low-profile EEG sensors are placed directly on the scalp without conductive gel or paste.

14. The method of claim 12, wherein the set of low-profile EEG sensors includes i) a reference array of flexible epidermis-penetrating microneedle electrodes placed at an apex position on the scalp and ii) six arrays of flexible epidermis-penetrating microneedle electrodes releasably attached to a low-modulus elastomeric band at a first frontal position, a second back position, and at four side positions for motor imagery measurements.

15. The method of claim 12, wherein the set of low-profile EEG sensors includes i) a reference array of flexible epidermis-penetrating microneedle electrodes placed at a back position on the scalp and ii) four arrays of flexible epidermis-penetrating microneedle electrodes releasably attached to a low-modulus elastomeric band at a back region of the scalp for steady-state visually evoked potentials (SSVEP) measurements.

16. The method of claim 12, further comprising:
transmitting, by the processor, the acquired EEG signals to a remote or cloud computing device executing a retraining operation of the trained neural network; and
receiving, by the processor, during run-time operation of the virtual reality environment controller an updated trained neural network from the remote or cloud computing device.

17. A non-transitory computer-readable medium having instructions stored thereon, wherein execution of the instructions by a processor of a brain-machine interface controller causes the processor to:
receive EEG signals acquired from a set of low-profile EEG sensors placed at a scalp of a user, wherein the set of low-profile EEG sensors each comprises an array of flexible epidermis-penetrating microneedle electrodes fabricated on a flexible-circuit substrate, the flexible-circuit substrate operatively connected to an analog-to-digital converter circuitry operatively connected to a wireless interface circuitry, wherein the set of low-profile EEG sensors are placed directly on the scalp without conductive gel or paste;
continuously classify brain signals as control signals via a trained neural network from the acquired EEG signals; and
output the control signals to a virtual reality environment controller to actuate a command in a VR scene generated by the virtual reality environment controller to be viewed by a subject.

18. The computer-readable medium of claim 17, wherein the set of low-profile EEG sensors includes i) a reference array of flexible epidermis-penetrating microneedle electrodes placed at an apex position on the scalp and ii) six arrays of flexible epidermis-penetrating microneedle electrodes releasably attached to a low-modulus elastomeric band at a first frontal position, a second back position, and at four side positions for motor imagery measurements.

19. The computer-readable medium of claim 17, wherein the set of low-profile EEG sensors includes i) a reference array of flexible epidermis-penetrating microneedle electrodes placed at a back position on the scalp and ii) four arrays of flexible epidermis-penetrating microneedle electrodes releasably attached to a low-modulus elastomeric band at a back region of the scalp for steady-state visually evoked potentials (SSVEP) measurements.

20. The computer-readable medium of claim 17, wherein the execution of the instructions further causes the processor to:
transmit the acquired EEG signals to a remote or cloud computing device executing a retraining operation of the trained neural network; and
receive during run-time operation of the virtual reality environment controller an updated trained neural network from the remote or cloud computing device.

* * * * *